United States Patent [19]
Talley et al.

[11] Patent Number: 5,643,924
[45] Date of Patent: Jul. 1, 1997

[54] RETROVIRAL PROTEASE INHIBITORS

[75] Inventors: John J. Talley; Daniel P. Getman, both of Chesterfield; Gary A. DeCrescenzo, St. Peters, all of Mo.; Kathryn L. Reed, Raleigh, N.C.; Ko-Chung Lin, St. Louis; John Nicholas Freskos, Clayton, both of Mo.; Michael Clare, Skokie, Ill.; Donald Joseph Rogier, Jr., St. Louis; Robert M. Heintz, Ballwin, both of Mo.; Michael L. Vazquez, Gurnee; Richard A. Mueller, Glencoe, both of Ill.

[73] Assignee: Monsanto Company of St. Louis, St. Louis, Mo.

[21] Appl. No.: 455,237

[22] Filed: May 31, 1995

Related U.S. Application Data

[62] Division of Ser. No. 886,700, May 12, 1992, abandoned.
[51] Int. Cl.$^6$ .................................................. A61K 31/44
[52] U.S. Cl. ..................... 514/307; 546/146; 546/147
[58] Field of Search ..................... 546/146, 147; 514/307

[56] References Cited

U.S. PATENT DOCUMENTS

| | | |
|---|---|---|
| H725 | 1/1990 | Gordon . |
| 4,450,164 | 5/1984 | Bristol et al. . |
| 4,477,441 | 10/1984 | Boger et al. . |
| 4,514,391 | 4/1985 | Gordon et al. . |
| 4,548,926 | 10/1985 | Matsueda et al. . |
| 4,599,198 | 7/1986 | Hoover ................................ 260/998.2 |
| 4,616,088 | 10/1986 | Ryono et al. . |
| 4,668,769 | 5/1987 | Hoover . |
| 4,668,770 | 5/1987 | Boger et al. . |
| 4,757,050 | 7/1988 | Natarajan et al. ......................... 514/18 |
| 4,880,938 | 11/1989 | Freidinger . |
| 4,963,530 | 10/1990 | Hemmi et al. . |
| 4,977,277 | 12/1990 | Rosenberg et al. ..................... 549/215 |

FOREIGN PATENT DOCUMENTS

| | | |
|---|---|---|
| 79823 | 4/1988 | Australia . |
| 0104041 | 3/1984 | European Pat. Off. . |
| 0114993 | 8/1984 | European Pat. Off. . |
| 264795 | 10/1986 | European Pat. Off. . |
| 223437 | 5/1987 | European Pat. Off. . |
| 337714 | 10/1989 | European Pat. Off. . |
| 342541 | 11/1989 | European Pat. Off. . |
| 346847 | 12/1989 | European Pat. Off. . |
| 356223 | 2/1990 | European Pat. Off. . |
| 389898 | 10/1990 | European Pat. Off. . |
| 393445 | 10/1990 | European Pat. Off. . |
| 393457 | 10/1990 | European Pat. Off. . |
| 480711 | 10/1990 | European Pat. Off. . |
| 402646 | 12/1990 | European Pat. Off. . |
| 480624 | 4/1992 | European Pat. Off. . |
| 480714 | 4/1992 | European Pat. Off. . |
| 2184730 | 7/1987 | United Kingdom . |
| 2200115 | 7/1988 | United Kingdom . |
| 2209752 | 5/1989 | United Kingdom . |
| PCT/WO84/03044 | 8/1984 | WIPO . |

OTHER PUBLICATIONS

Drugs of the Future, 1991, 16(3):210–212.

Nature, vol. 328, No. 6130, Aug. 6–12, 1987, p. 482.

Pept. Struct. Funct. Proc. Am. Pept. Sym. 8th ed. by V.J. Hunby and D.H. Rich (1983) pp. 511–520.

Roberts, et al., "Rational Design of Peptide–Based HIV Proteinase Inhibitors," *Science*, 248, 358 (1990).

Erickson et al., "Design Activity and 2.8 Å Crystal Structure of a $C_2$ Symmetric Inhibitor Complexed to HIV–1 Protease," *Science*, 249, 527 (1990).

Meek, et al., "Inhibition of HIV–1 Protease in Infected T–lymphocytes by Synthetic Peptide Analogues," *Nature*, 343, 90 (1990).

McQuade, et al., "A Synthetic HIV–1 Protease Inhibitor With Antiviral Activity Arrests HIV–Like Particle Maturation," *Science*, 247, 454 (1990).

*Primary Examiner*—Samuel Barts
*Attorney, Agent, or Firm*—Frank S. Ungemach

[57] ABSTRACT

N-heterocyclic moiety containing hydroxyethylamine compounds are effective as retroviral protease inhibitors, and in particular as inhibitors of HIV protease.

66 Claims, No Drawings

RETROVIRAL PROTEASE INHIBITORS

This is a divisional of application Ser. No. 07/886,700, filed May 21, 1992, now abandoned.

BACKGROUND OF THE INVENTION

1. Field of the Invention

The present invention relates to retroviral protease inhibitors and, more particularly, relates to novel compounds and a composition and method for inhibiting retroviral proteases. This invention, in particular, relates to N-heterocyclic moiety-containing hydroxyethylamine protease inhibitor compounds, a composition and method for inhibiting retroviral proteases such as human immunodeficiency virus (HIV) protease and for treatment or prophylaxis of a retroviral infection, e.g., an HIV infection. The subject invention also relates to processes for making such compounds as well as to intermediates useful in such processes.

2. Related Art

During the replication cycle of retroviruses, gag and gag-pol gene products are translated as proteins. These proteins are subsequently processed by a virally encoded protease (or proteinase) to yield viral enzymes and structural proteins of the virus core. Most commonly, the gag precursor proteins are processed into the core proteins and the pol precursor proteins are processed into the viral enzymes, e.g., reverse transcriptase and retroviral protease. It has been shown that correct processing of the precursor proteins by the retroviral protease is necessary for assembly of infectious virons. For example, it has been shown that frameshift mutations in the protease region of the pol gene of HIV prevents processing of the gag precursor protein. It has also been shown through site-directed mutagenesis of an aspartic acid residue in the HIV protease that processing of the gag precursor protein is prevented. Thus, attempts have been made to inhibit viral replication by inhibiting the action of retroviral proteases.

Retroviral protease inhibition typically involves a transition-state mimetic whereby the retroviral protease is exposed to a mimetic compound which binds (typically in a reversible manner) to the enzyme in competition with the gag and gag-pol proteins to thereby inhibit replication of structural proteins and, more importantly, the retrovixal protease itself. In this manner, retroviral proteases can be effectively inhibited.

Several classes of mimetic compounds are known to be useful as inhibitors of the proteolytic enzyme renin. See, for example, U.S. Pat. No. 4,599,198; G.B. 2,184,730; G.B. 2,209,752; EP 0 264 795; G.B. 2,200,115 and U.S. SIR H725. Of these, G.B. 2,200,115; G.B 2,209,752; EP 0 264,795; U.S. SIR H725; and U.S. Pat. No. 4,599,198 disclose urea-containing hydroxyethylamine renin inhibitors. However, it is known that, although renin and HIV proteases are both classified as aspartyl proteases, compounds which are effective renin inhibitors generally cannot be predicted to be effective HIV protease inhibitors.

Several classes of mimetic compounds have been proposed, particularly for inhibition of proteases, such as for inhibition of HIV protease. Such mimetics include hydroxyethylamine isoteres and reduced amide isosteres. See, for example, EP 0 346 847; EP 0 342,541; Roberts et al, "Rational Design of Peptide-Based Proteinase Inhibitors," *Science*, 248, 358 (1990); and Erickson et at, "Design Activity, and 2.8Å Crystal Structure of a C₂ Symmetric Inhibitor Complexed to HIV-1 Protease," *Science*, 249, 527 (1990). EP 0 346 847 discloses certain N-heterocyclic moiety-containing hydroxyethylamine protease inhibitor compounds, but does not suggest or disclose those of the present invention.

While it has been suggested that no improvement in the in vitro or ex vivo potency of hydroxyethyl-amine based inhibitors of HIV-protease containing a $P_2$ asparagine can be made (*Science*, Roberts et al.), we find that this is not the case. Not only have we made in vitro and ex vivo improvements over $P_2$ asparagine containing inhibitors, but the novel moieties reported herein are expected to permit certain allowances over the aforementioned reference including proteolytic stability, duration of action in vivo and pharmacokinetic profile.

BRIEF DESCRIPTION OF THE DRAWINGS

The present invention is directed to virus inhibiting compounds and compositions. More particularly, the present invention is directed to retroviral protease inhibiting compounds and compositions, to a method of inhibiting retroviral proteases, to processes for preparing the compounds and to intermediates useful in such processes. The subject compounds are characterized as N-heterocyclic moiety-containing hydroxyethylamine inhibitor compounds.

DETAILED DESCRIPTION OF THE PREFERRED EMBODIMENTS

In accordance with the present invention, there are provided several novel retroviral protease inhibiting compounds or a pharmaceutically acceptable salt, prodrug or ester thereof.

A preferred class of retroviral inhibitor compounds of the present invention are those represented by the formula

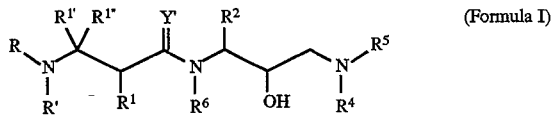
(Formula I)

or a pharmaceutically acceptable salt, prodrug or ester thereof, wherein the stereochemistry about the hydroxy group is designated as (R) and wherein:

R represents hydrogen, alkoxycarbonyl, aryloxycarbonyl alkyl, aralkoxy-carbonyl, alkylcarbonyl, cycloalkylcarbonyl, cycloalkylalkoxycarbonyl, cycloalkylalkanoyl, alkanoyl, aralkanoyl, aroyl, aryloxycarbanoyl, aryloxyalkanoyl, heterocyclylcarbonyl, heterocycloxycarbonyl, heteroaralkoxycarbonyl, heterocyclylalkanoyl, heterocyclylalkoxycarbonyl, heteroarylcarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aralkylaminoalkylcarbonyl, aminoalkanoyl, aminocarbonyl, aminocarbonylalkyl, alkylaminoalkylcarbonyl, and mono- and disubstituted aminocarbonyl and aminoalkanoyl radicals wherein the substituents are selected from the group consisting of alkyl, aryl, aralkyl, cycloalkyl, cycloalkylalkyl, heteroaryl, heteroaralkyl, heterocycloalkyl, and heterocycloalkylalkyl radicals, or in the case of disubstituted aminoalkanoyl, said substituents along with the nitrogen atom to which they are attached form a heterocyclyl or heteroaryl radical;

R' represents radicals defined for $R^3$, or R and R' together with the nitrogen to which they are attached form a heterocycloalkyl or heteroaryl radical;

$R^1$ represents hydrogen, —$CH_2SO_2NH_2$, —$CO_2CH_3$, —$CH_2CO_2CH_3$, —$C(O)N_2$, —$C(O)NHCH_3$, —$C(O)N(CH_3)_2$, —$CH_2C(O)NHCH_3$, —$CH_2C(O)N(CH_3)_2$, alkyl, thiolalkyl and the corresponding sulfoxide and sulfone derivatives thereof, alkenyl, alkynyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allo-threonine, serine, aspartic acid and beta-cyano alanine, side chains;

$R^{1'}$ and $R^{1''}$ independently represent hydrogen and radicals as defined for $R^1$, or one of $R^{1'}$ and $R^{1''}$ together with $R^1$ and the carbon atoms to which they are attached represent a cycloalkyl radical;

$R^2$ represents alkyl, aryl, cycloalkyl, cycloalkylalkyl and aralkyl radicals, which radicals are optionally substituted with a substituent selected from the group consisting of —$NO_2$, —$OR^{15}$, —$SR^{15}$, and halogen radicals, wherein $R^{15}$ represents hydrogen and alkyl radicals;

$R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

Y' represents O, S and $NR^3$;

$R^4$ and $R^5$ together with the nitrogen atom to which they are bonded represent a N-heterocyclic moiety; and $R^6$ represents hydrogen and alkyl radicals.

Another class of preferred inhibitor compounds of the present invention are those represented by the formula:

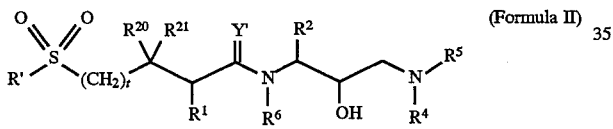

(Formula II)

or a pharmaceutically acceptable salt, prodrug or ester thereof, wherein:

R' represents radicals as defined for $R^3$ and arlkoxycarbonylalkyl and aminocarbonyl radicals wherein said amino group may be mono- or disubstituted with substituents selected from alkyl, aryl, aralkyl, cycloalkyl, cycloalkylalkyl, heteroaryl, heteroaralkyl, heterocycloalkyl and heterocycloalkyl alkyl radicals;

t represents either 0 or 1;

$R^1$ represents hydrogen, —$CH_2SO_2NH_2$, —$CO_2CH_3$, —$CH_2CO_2CH_3$, —$C(O)NH_2$, —$C(O)NHCH_3$, —$C(O)N(CH_3)_2$, —$CH_2C(O)NHCH_3$, —$CH_2C(O)N(CH_3)_2$, alkyl, thioalkyl and the corresponding sulfoxide and sulfone derivatives thereof, alkenyl, alkynyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allo-threonine, serine, aspartic acid and beta-cyano alanine side chains;

$R^2$ represents alkyl, aryl, cycloalkyl, cycloalkylalkyl and aralkyl radicals, which radicals are optionally substituted with a substituent selected from the group consisting of —$NO_2$, —$OR^{15}$, —$SR^{15}$, and halogen radicals, wherein $R^{15}$ represents hydrogen and alkyl radicals;

$R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

Y' represents O, S and $NR^3$;

$R^4$ and $R^5$ together with the nitrogen atom to which they are bonded represent a N-heterocyclic moiety;

$R^6$ represents hydrogen and alkyl radicals; and $R^{20}$ and $R^{21}$ represent radicals as defined for $R^1$.

Yet another preferred class of compounds of the present invention are those represented by the formula:

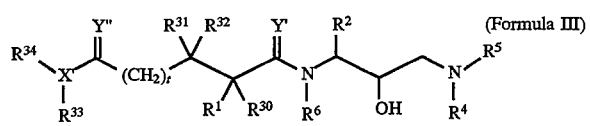

(Formula III)

or a pharmaceutically acceptable salt, prodrug or ester thereof, wherein:

t represents either 0 or 1;

$R^1$ represents hydrogen, —$CH_2SO_2NH_2$, —$CO_2CH_3$, —$CH_2CO_2CH_3$, —$C(O)NH_2$, —$C(O)NHCH_3$, —$C(O)N(CH_3)_2$, —$CH_2(O)NHCH_3$, —$CH_2(O)N(CH_3)_2$, alkyl, thioalkyl and the corresponding sulfoxide and sulfone derivatives thereof, alkenyl, alkynyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allo-threonine, serine, aspartic acid and beta-cyano alanine side chains;

$R^2$ represents alkyl, aryl, cycloalkyl, cycloalkylalkyl and aralkyl radicals, which radicals are optionally substituted with a substituent selected from the group consisting of —$NO_2$, —$OR^{15}$, —$SR^{15}$, and halogen radicals, wherein $R^9$ represents hydrogen and alkyl radicals;

$R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

X' represent O, N and $C(R^{17})$ where $R^{17}$ represents hydrogen and alkyl radicals;

Y' and Y" independently represent O, S and $NR^3$;

$R^4$ and $R^5$ together with the nitrogen atom to which they are bonded represent a N-heterocyclic moiety;

$R^6$ represents hydrogen and alkyl radicals;

$R^{30}$, $R^{31}$ and $R^{32}$ independently represent radicals as defined for $R^1$, or one of $R^1$ and $R^{30}$ together with one of $R^{31}$ and $R^{32}$ and the carbon atoms to which they are attached form a cycloalkyl radical; and $R^{33}$ and $R^{34}$ independently represent radicals as defined for $R^3$, or $R^{33}$ and $R^{34}$ together with X' represent cycloalkyl, aryl, heterocyclyl and heteroaryl radicals, provided that when X' is O, $R^{34}$ is absent.

Still another preferred class of compounds of the present invention are those represented by the formula:

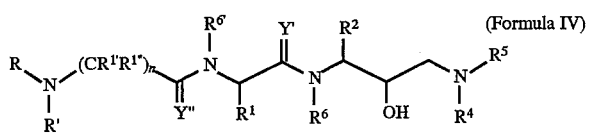

(Formula IV)

or a pharmaceutically acceptable salt, prodrug or ester thereof, wherein:

R represents hydrogen, alkyl, alkenyl, cycloalkyl, aryl, aralkyl, aryloxyalkyl, heteroaryl, heterarylalkyl, heteroaryloxyalkyl and hydroxyalkyl;

R' represents radicals defined for $R^3$, or R and R' together with the nitrogen to which they are attached form a heterocycloalkyl or heteroaryl radical;

n represents 1 or 2;

$R^1$ represents hydrogen, —$CH_2SO_2NH_2$, —$CO_2CH_3$, —$CH_2CO_2CH_3$, —$C(O)NH_2$, —$C(O)NHCH_3$, —$C(O)N(CH_3)_2$, —$CH_2C(O)NHCH_3$, —$CH_2C(O)N(CH_3)_2$, alkyl, thioalkyl and the corresponding sulfoxide and sulfone derivatives thereof, alkenyl, alkynyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allo-threonine, serine, aspartic acid and beta-cyano alanine side chains;

$R^{1'}$ and $R^{1''}$ independently represent hydrogen and radicals as defined for $R^1$.

$R^2$ represents alkyl, aryl, cycloalkyl, cycloalkylalkyl and aralkyl radicals, which radicals are optionally substituted with a substituent selected from the group consisting of —$NO_2$, —$OR^{15}$, —$SR^{15}$, and halogen radicals, wherein $R^{15}$ represents hydrogen and alkyl radicals;

$R^3$ represents hydrogen, alkyl, alkenyl, alkynyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

Y' and Y'' independently represent O, S and $NR^3$;

$R^4$ and $R^5$ together with the nitrogen atom to which they are bonded represent a N-heterocylic moiety;

$R^6$ and $R^{6'}$ independently represent hydrogen and alkyl radicals.

As utilized herein, the term "alkyl", alone or in combination, means a straight-chain or branched-chain alkyl radical containing from 1 to about 10, preferably from 1 to about 8, carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "thioalkyl" means an alkyl radical having at least one sulfur atom, wherein alkyl has the significance given above. An example of a thioalkyl is —$C(CH_3)_2SCH_3$. The corresponding sulfoxide and sulfone of this thioalkyl are —$C(CH_3)_2S(O)CH_3$ and —$C(CH_3)_2S(O)_2CH_2$, respectively. The term "alkenyl", alone or in combination, means a straight-chain or branched-chain hydrocarbon radial having one or more double bonds and containing from 2 to about 18 carbon atoms preferably from 2 to about 8 carbon atoms. Examples of suitable alkenyl radicals include ethenyl, propenyl, allyl, 1,4-butadienyl and the like. The term "alkynyl", alone or in combination, means a straight-chain hydrocarbon radical having one or more triple bonds and containing from 2 to about 10 carbon atoms. Examples of alkynl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like. The term "cycloalkylalkyl" means an alkyl radical as defined above which is substituted by a cycloalkyl radical containing from about 3 to about 8, preferably from about 3 to about 6, carbon atoms. The term "aryl", alone or in combination, means a phenyl or naphthyl radical which optionally carries one or more substituents selected from alkyl, alkoxy, halogen, hydroxy, amino, nitro and the like, such as phenyl, p-tolyl, 4-methoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aralkoxy carbonyl", alone or in combination, means a radical of the formula —C(O)—O—aralkyl in which the term "aralkyl" has the significance given above. An example of an aralkoxycarbonyl radical is benzyloxycarbonyl. The term "aryloxy", alone or in combination, means a radical of the formula aryl-O— in which the term "aryl" has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3, 4-tetrahydro-2-naphthoyl, 2-acetamido-1,2,3,4-tetrahydro-2-naphthoyl. The term "aralkanoyl" means an acyl radical derived from an aryl-substituted alkanecarboxylic acid such as phenylacetyl, 3-phenylpropionyl (hydrocinnamoyl, 4-phenylbutyryl, (2-naphthyl)acetyl, 4-chlorohydrocinnamoyl, 4-aminohydrocinnamoyl, 4-methoxyhydrocinnamoyl, and the like. The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The heterocyclyl or heterocycloalkyl portion of a heterocyclylcarbonyl, heterocyclyloxycarbonyl, heterocyclylalkoxycarbonyl, or heterocyclylalkyl group or the like is a saturated or partially unsaturated monocyclic, bicyclic or tricyclic heterocycle which contains one or more hetero atoms selected from nitrogen, oxygen and sulphur, which is optionally substituted on one or more carbon atoms by halogen, alkyl, alkoxy, oxo, and the like, and/or on a secondary nitrogen atom (i.e., —NH—) by alkyl, aralkoxycarbonyl, alkanoyl, phenyl or phenylalkyl or on a tertiary nitrogen atom (i.e. =N—) by oxido and which is attached via a carbon atom. The heteroaryl potion of a heteroaroyl, heteroaralkoxycarbonyl, or heteroaralkoxycarbonyl group or the like is an aromatic monocyclic, bicyclic, or tricyclic heterocyle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiamorpholinyl, pyrrolyl, imidazolyl (e.g., imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g., 2-indolyl, etc.), quinolinyl (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolinyl, etc. ), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-, 2-, 4- or 5-benzimidazolyl, and the like. The term "cycloalkylalkoxycarbonyl" means an acyl group derived from a cycloalkylalkoxycarboxylic acid of the formula cycloalkylalkyl-O-COOH wherein cycloalkylalkyl has the significance given above. The term "aryloxyalkanoyl" means an acyl radical of the formula aryl-O-alkanoyl wherein aryl and alkanoyl have the significance given above. The term "heterocyclylalkanoyl" is an acyl radical derived from a heterocyclyl-substituted alkane carboxylic acid wherein heterocyclyl has the significance given above. The term "heterocyclyloxycarbonyl" means an acyl group derived from heterocyclyl-O-COOH wherein heterocyclyl is as defined above. The term "heterocyclylalkanoyl" means an acyl radical of the formula aryl-O-alkanoyl wherein aryl and alkanoyl have the significance given above. The term "heterocyclylalkoxycarbonyl" means an acyl radical derived from heterocyclyl-substituted alkane-O-COOH wherein heterocyclyl has the significance given above. The term "heteroaryloxycarbonyl" means an acyl radical derived from a carboxylic acid represented by heteraryl-O-COOH wherein heteroaryl has the significance given above. The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, and alkyl, aryl, aralkyl, cycloalkyl, cycloalkylalkyl radicals and the like. The term "aminoalkanoyl" means an acyl radical derived from an amino substituted alkanecarboxylic acid wherein the amino group can be a primary, secondary or tertiary amino group containing substituents selected from the group consisting of hydrogen cycloalkyl, cycloalkylalkyl radicals and the like, examples of which include N,N-dimethylaminoacetyl and N-benzylaminoacetyl. The term "halogen" means fluorine, chlorine, bromine or iodine. The term "leaving group" generally refers to groups readily displaceable by a nucleophile, such as an mine, a thiol or an alcohol nucleophile. Such leaving groups are well known and include carboxylates, N-hydroxysuccinimide, N-hydroxybenzotriazole, halides, triflates, tosylates, —OR and —SR and the like. Preferred leaving groups are indicated herein where appropriate. The term "N-heterocyclic moiety" is a heterocyclic radical with a nitrogen radical bond site which may be a heterocycloalkyl or heteroaryl, wherein heterocycloalkyl and hetearyl have the significance given above, with the addition that polycyclic heteroaryl may be fully aromatic or partially aromatic, for example, a fused heterocycloalkylaryl and a fused heteroarylcycloalkyl, and the heterocycloalkyl and cycloalkyl may also be bridged. Preferably, the N-heterocyclic moiety has 5, 6 or 7 members when monocyclic; 5, 6 or 7 members in a ring with 1, 2 or 3 members in a bridge when a bridged monocyclic; 11, 12 or 13 members when bicyclic; and 11 to 16 members when tricyclic.

Examples of N-heterocyclic moieties include, but are not limited to, those represented by the following formulas:

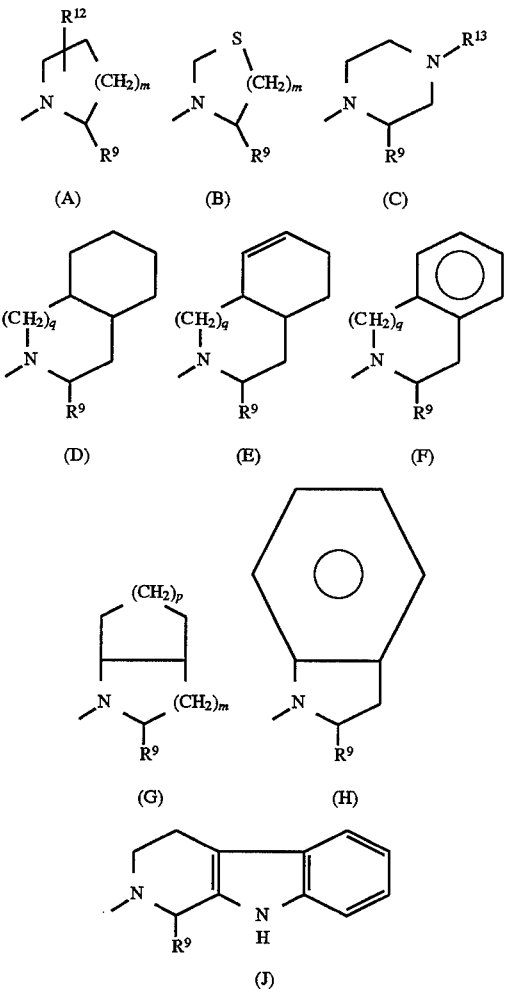

wherein:

$R^9$ represents hydrogen, alkyl, alkylcarbonyl, monoalkylcarbamoyl, monoaralkylcarbamoyl, monoarylcarbamoyl or a group of the formula:

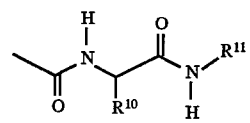

wherein $R^{10}$ and $R^{11}$ each represents alkyl;

$R^{12}$ represents hydrogen, hydroxy, alkoxycarbonylamino or acylamino;

$R^{13}$ represents hydrogen, alkyl, aryl, alkoxycarbonyl or acyl;

m is 1, 2, 3, or 4;

p is 1 or 2; and q is 0, 1 or 2.

Procedures for preparing the compounds of Formulas I–IV are set forth below. R should be noted that the general procedure is shown as it relates to preparation of compounds having the specified stereochemistry, for example, wherein the stereochemistry about the hydroxyl group is designated as (R). However, such procedures are generally applicable to those compounds of opposite configuration, e.g., where the stereochemistry about the hydroxyl group is (S). The terms (R) and (S) configuration are as defined by the IUPAC 1974 Recommendations for Section E, Fundamental Stereochemistry, Pure Appl. Chem. (1976) 45, 13–30.

Preparation of Compounds of Formula I

The compounds of the present invention represented by Formula I above can be prepared utilizing the following general procedure. An N-protected haloketone derivative of an amino acid having the formula:

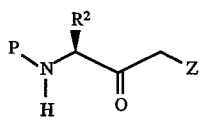

wherein P represents an amino protecting group, $R^2$ is as defined above and Z represents a chlorine, bromine or iodine atom, is reduced to the corresponding alcohol utilizing an appropriate reducing agent. Suitable amino protecting groups are well known in the art and include carbobenzoxy, butyryl, t-butoxycarbonyl, acetyl, benzoyl and the like. Preferred amino protecting groups are carbobenzoxy and t-butoxycarbonyl. A preferred N-protected haloketone is N-benzyloxycarbonyl-L-phenylalanine chloromethyl ketone. A preferred reducing agent is sodium borohydride. The reduction reaction is conducted at a temperature of from —10° C. to about 25° C., preferably at about 0° C., in a suitable solvent system such as, for example, tetrahydrofuran, and the like. The N-protected haloketones are commercially available from Bachem, Inc., Torrance, Calif. Alternatively, the haloketones can be prepared by the procedure set forth in S. J. Fittkau, J. Prakt. Chem., 315, 1037 (1973), and subsequently N-protected utilizing procedures which are well known in the art.

The resulting alcohol is then reacted, preferably at room temperature, with a suitable base in a suitable solvent system to produce an N-protected amino epoxide of the formula:

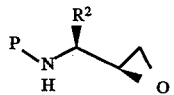

wherein P and $R^2$ are as defined above. Suitable solvent systems for preparing the amino epoxide include methanol, ethanol, isopropanol, tetrahydrofuran, dioxane, and the like including mixtures thereof. Suitable bases for producing the epoxide from the reduced haloketone include potassium hydroxide, sodium hydroxide, potassium t-butoxide, DBU and the like. A preferred base is potassium hydroxide.

Alternatively, a protected amino epoxide can be prepared starting with an L-amino acid which is reacted with a suitable amino- and carboxyl-protecting groups in a suitable solvent to produce an amino-protected L-amino acid ester of the formula:

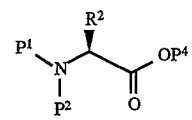

wherein $P^1$ and $P^2$ independently represent hydrogen and amino-protecting groups as defined above with respect to P, provided that $P^1$ and $P^2$ are not both hydrogen; $P^4$ represents hydrogen and a carboxy-protecting group, preferably one which is also an amino-protecting group as defined above with respect to P; and $R^2$ is as defined above.

The amino-protected L-amino acid ester is then reduced, to the corresponding alcohol. For example, the amino-protected L-amino acid ester can be reduced with diisobutylaluminum hydride at –78° C. in a suitable solvent such as toluene. The resulting alcohol is then converted, by way of a Swern Oxidation, to the corresponding aldehyde of the formula:

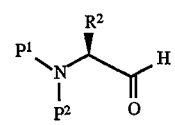

wherein $P^1$, $P^2$ and $R^2$ are as defined above. Thus, a dichloromethane solution of the alcohol is added to a cooled (–75° to –68° C.) solution of oxalyl chloride in dichloromethane and DMSO in dichloromethane and stirred for 35 minutes.

The aldehyde resulting from the Swern Oxidation is then reacted with a halomethyllithium reagent, which reagent is generated in situ by reacting an alkyllithium or aryllithium compound with a dihalomethane represented by the formula $X^1CH_2X^2$ wherein $X^1$ and $X^2$ independently represent I, Br or Cl. For example, a solution of the aldehyde and chloriodomethane in THF is cooled to –78° C. and a solution of n-butyllithium in hexane is added. The resulting product is a mixture of diastereomers of the corresponding aminoprotected epoxides of the formulas:

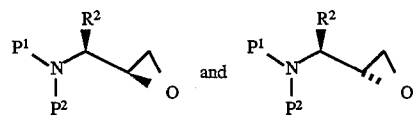

The diastereomers can be separated by chromatography or, alternatively, once reacted in subsequent stops the distereomeric products can be separated.

The amino epoxide is then reacted, in a suitable solvent system, with an equal amount, of the formula:

HNR⁴R⁵ wherein $R^4$ and $R^5$ are as defined above. The reaction can be conducted over a wide range of temperatures, e.g., from about 60° C. to about 120° C. in an inert organic solvent, but is preferably, but not necessarily, conducted at a temperature at which the solvent begins to reflux. Suitable solvent systems include those wherein the solvent is an alcohol, such as methanol, ethanol, isopropanol, and the like, ethers such as tetrahydrofuran, dioxane and the like, toluene, N,N-dimethylformamide, dimethyl sulfoxide, and mixtures thereof. A preferred solvent is isopropanol. Examples of amines corresponding to the formula $HNR^4R^5$ include those having the following formula:

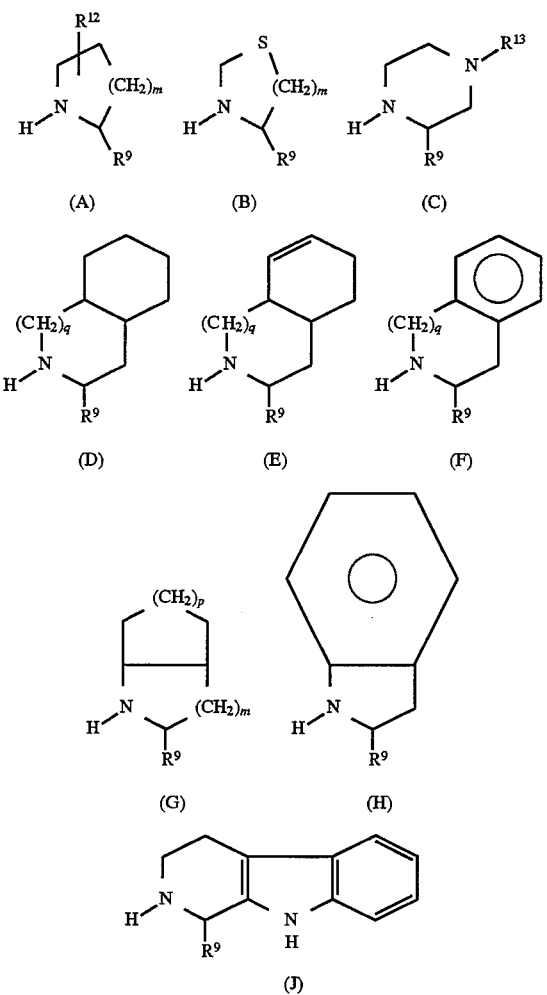

wherein:

$R^9$, $R^{10}$, $R^{11}$, $R^{12}$, $R^{13}$, m, p and q have the significance given above, and the like. The resulting product is a 3-(N-protected amino)-3-$(R^2)$-1-$(NR^4R^5)$-propan-2-ol derivative (hereinafter referred to as an amino alcohol) is an intermediate which contains the desired N-heterocyclic moiety or intermediate thereof and can be represented by the formula:

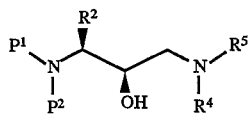

wherein $P^1$, $P^2$, $R^2$, $R^4$ and $R^5$ are as described above.

Alternatively, the compounds of the present invention represented by Formula I above can be prepared utilizing the following general procedure. An N-protected haloketone derivative of an amino acid having the formula:

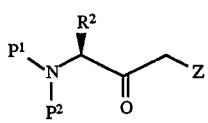

wherein $P^1$ and $P^2$ represent amino protecting groups, $R^2$ is as defined above, and Z represents a chlorine, bromine or iodine atom, is reacted, in a suitable inert organic solvent system, with an equal amount, of a desired amine of the formula:

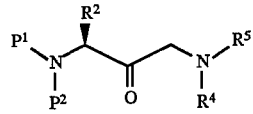

wherein $R^4$ and $R^5$ are as defined above. The reaction yields a compound of the general formula:

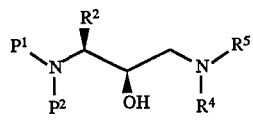

(Formula V)

wherein $P^1$, $P^2$, $R^2$, $R^4$ and $R^5$ have the significance given earlier.

The reaction of the N-protected haloketone derivative of an amino acid, preferably one in which $P^1$ and $P^2$ represent benzyloxy carbonyl, with the desired amine, a heterocyclic compound of formula $HNR^4R^5$, can be carried out in any known manner, for example, in an inert organic solvent such as halogenated aliphatic hydrocarbon (e.g. dichloromethane, N,N-dimethylformamide, tetrahydrofuran, isopropanol and ethanol) and in the presence of a base (e.g. a trialkylamine such as triethylamine and diisopropylethyl amine, sodium bicarbonate, DBU and the like), conveniently at about room temperature.

The reduction of the aminoketone compound of Formula V results in a compound of the general formula:

(Formula VI)

wherein $P^1$, $P^2$, $R^2$, $R^4$ and $R^5$ have the significance given earlier. The reduction of the aminoketone compound of Formula V to the N-heterocyclic moiety-containing derivative (Formula VI) can be carried out according to known methods for the reduction of a carbonyl group to a hydroxy group. Thus, for example, the reduction can be carried out using a complex metal hydride such as an alkali metal borohydride, especially sodium borohydride, in an appropriate organic solvent such as alkanol (e.g. methanol, ethanol, propanol, isopropanol etc.). Conveniently, the reduction is carried out at about room temperature.

Following preparation of the N-heterocyclic moiety-containing derivative, the amino protecting group P is, or $P^1$ and $P^2$ are, removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is N,N-dibenzyl, these groups may be removed by hydrogenolysis utilizing palladium on carbon. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then meted with an amino acid or corresponding derivative thereof represented by the formula $(PNH[CR^1R^{1'}]CH(R^1)COOH)$ wherein $R^1$, $R^{1'}$ and $R^{1''}$ are as defined above, to produce the antiviral compounds of the present invention having the formula:

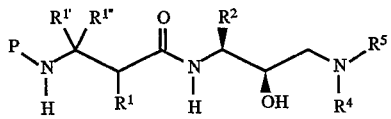

wherein P, $R^1$, $R^{1'}$, $R^{1''}$, $R^2$, $R^4$ and $R^5$ are as defined above. Preferred protecting groups in this instance are a benzyloxycarbonyl group or a t-butoxycarbonyl group. Where the amine is reacted with a derivative of an amino acid and $R^{1'}$ and $R^{1''}$ are both hydrogen, so that the amino acid is β-amino acid, such β-amino acids can be prepared according to the procedure set forth in copending applications, U.S. Ser. No. 07/836,163 (Method of Preparing Optically Active β-Amino Acids; filed Feb. 14, 1992; (a continuation of U.S. Ser. No. 07/706,508, now abandoned, which is a continuation of U.S. Ser. No. 07/345,808, now abandoned). Where one of $R^{1'}$ and $R^{1''}$ is hydrogen and $R^1$ is hydrogen so that the amino acid is a homo-β-amino acid, such homo-β-amino acids can be prepared according to the procedure set forth in copending application, U.S. Ser. No. 07/853,561 (Method of Preparing Optically Active Homo-β-Amino Acids. The process thereof preserves the chirality of the starting succinates. The method thereof involves Curtis rearrangement of chiral 3-monosubstituted succinates (succinic acid half ester) of sufficient purity to exhibit optical activity. The Curtis rearrangement is preferably effected by treating a chiral 3-mono-substituted succinate with one equivalent of diphenoxyphosphoryl azide $(PhO)_2PON_3$ and triethylamine to form an acyl azide followed by heating in an inert solvent, such as warm toluene, preferably at about 80° C. for about three hours to afford an isocyanate derivative which is subsequently hydrolyzed to give mines. The 3-mono-substituted succinates can be prepared by a procedure analogous to that described in U.S. Pat. No. 4,939,288, filed Jan. 23, 1989, which is hereby incorporated by reference.

The N-protecting group can be subsequently removed, if desired, utilizing the procedures described above, and then reacted with a carboxylate represented by the formula:

wherein R is as defined above and L is an appropriate leaving group such as a halide. Examples of such carboxylates include acetylchloride, phenoxyacetyl chloride, benzoyl chloride, 2-naphthyloxy carbonyl chloride, and 2-benzofuran carbonyl chloride. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Alternatively, a sulfonyl-containing compound represented by the formula:

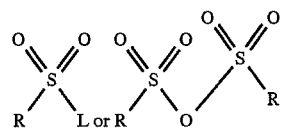

wherein R is as defined above and L is an appropriate leaving group such as halide may be substituted for the afore-mentioned carboxylate.

Preparation of Compounds of Formula II

A mercaptan of the formula R'SH is reacted with a substituted methacrylate of the formula:

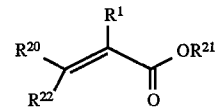

by way of a Michael Addition. The Michael Addition is conducted in a suitable solvent and in the presence of a suitable base, to produce the corresponding thiol derivative represented by the formula:

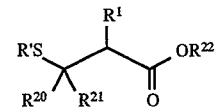

wherein R' and $R^1$ represent radicals defined above; $R^{20}$ and $R^{21}$ represent hydrogen and radicals as defined for $R^1$; and $R^{22}$ represents alkyl, aryl or aralkyl, preferably $R^{22}$ is methyl, ethyl, t-butyl or benzyl. Suitable solvents in which the Michael Addition can be conducted include alcohols such as, for example, methanol, ethanol, butanol and the like, as well as ethers, e.g., THF, and acetonitrile, DMF, DMSO, and the like, including mixtures thereof. Suitable bases include Group I metal alkoxides such as, for example sodium methoxide, sodium ethoxide, sodium butoxide and the like as well as Group I metal hydrides, such as sodium hydride, including mixtures thereof.

The thiol derivative is convened into the corresponding sulfone of the formula:

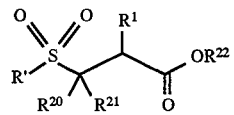

by oxidizing the thiol derivative with a suitable oxidation agent in a suitable solvent. Suitable oxidation agents include, for example, hydrogen peroxide, sodium metaperborate, oxone (potassium peroxy monosulfate), meta-chloroperoxybenzoic acid, and the like, including mixtures thereof. Suitable solvents include acetic acid (for sodium meta-perborate) and, for other peracids, ethers such as THF and dioxane, and acetonitrile, DMF and the like, including mixtures thereof.

The sulfone is then converted to the corresponding free acid of the formula:

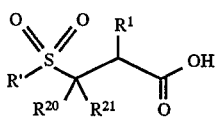

utilizing a suitable base, e.g., lithium hydroxide, sodium hydroxide, and the like, including mixtures thereof, in a suitable solvent, such as, for example, THF, acetonitrile, DMF, DMSO, methylene chloride and the like, including mixtures thereof. When $R^{22}$ is benzyl, the free acid may be obtained by hydrogenolysis over palladium on carbon.

The free acid is then coupled, utilizing, as described above, procedures well known in the art, to the N-heterocyclic moiety-containing derivative of an amino alcohol which is described above for the preparation of compounds of Formula I. The resulting product is a compound represented by Formula II.

Alternatively, one can couple the N-heterocyclic moiety-containing derivative to the commercially available acid,

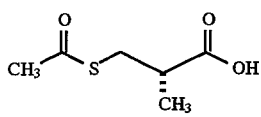

remove the thioacetyl group with a suitable base, such as hydroxide, or an amine, or ammonia, and then react the resulting thiol with an alkylating agent, such as an alkyl halide, tosylate or mesylate to afford compounds at the following structure:

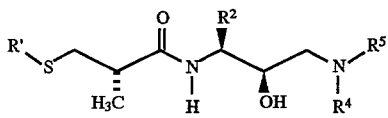

The sulfur can then be oxidized to the corresponding sulfone using suitable oxidizing agents, as described above, to afford the desired compounds of the following structure:

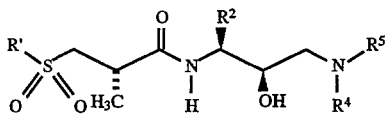

Alternatively, to prepare compounds of Formula II, a substituted methacrylate of the formula:

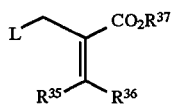

wherein L represents a leaving group as previously defined, $R^{35}$ and $R^{36}$ represent hydrogen and radicals as defined for $R^1$; and $R^{37}$ represents alkyl, aralkyl, cycloalkyl and cycloalkylalkyl radicals, is reacted with a suitable sulfonating agent, such as, for example, a sulfinic acid represented by the formula R'SO$_2$M, wherein R' represents radicals as defined above and M represents a metal adapted to form a salt of the acid, e.g., sodium, to produce the corresponding sulfone represented by the formula:

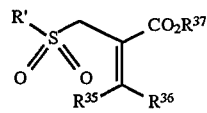

wherein R', $R^{35}$, $R^{36}$ and $R^{37}$ are as defined above. The sulfone is then hydrolyzed in the presence of a suitable base, such as lithium hydroxide, sodium hydroxide and the like, to the compound represented by the formula:

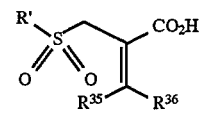

wherein R', $R^{35}$ and $R^{36}$ represent radicals as defined above. The resulting compound is then asymmetrically hydrogenated utilizing an asymmetric hydrogenation catalyst such as, for example, a ruthenium-BINAP complex, to produce the reduced product, substantially enriched in the more active isomer, represented by the formula:

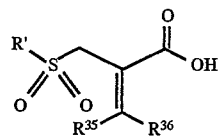

wherein R', $R^{35}$ and $R^{36}$ represent radicals as defined above. Where the more active isomer has the R-stereochemistry, a Ru(R-BINAP) asymmetric hydrogenation catalyst can be utilized. Conversely, where the more active isomer has the S-stereochemistry, a Ru(S-BINAP) cataylst can be utilized. Where both isomers are active, or where it is desired to have a mixture of the two diastereomers, a hydrogenation catalyst such as platinum, or palladium, on carbon can be utilized to reduce the above compound. The reduced compound is then coupled to the N-heterocyclic moiety-containing derivative, as described above, to produce compounds of Formula II.

Alternatively, one can prepare the preferred 2(S)-methyl-3-(methylsulfonyl)propionic acid according to the scheme outlined below starting from commercially available D-(−)-S-benzyoyl-beta-mercaptoisobutyric acid tert-butyl ester. Treatment of D-(−)-S-benzyoyl-beta-mercaptoisobutyric acid tert-butyl ester with a methanolic ammonia solution resulted in the formation of D-(−)-beta-mercaptoisobutyric acid tert-butyl ester and benzamide. The free mercaptan thus produced was freed from the benzamide by filtration and then further purified by crystallization. Treatment of D-(−)-beta-mercaptoisobutyric acid tert-butyl ester with methyl iodide in the presence of a suitable base such as 1,8-diazabicyclo[5.4.0]undec-7-ene (DBU) results in the formation of the corresponding thioether S-methyl-D-(−)-beta-mercaptoisobutyric acid tert-butyl ester in excellent yield. The thioether is then oxidized with a suitable oxidant such as sodium metaperborate in acetic acid to give the corresponding sulfone. Specifically, S-methyl-D-(−)-beta-mercaptoisobutyric acid tert-butyl ester is treated with sodium perborate in acetic acid to produce 2(S)-methyl-3-(methylsulfonyl)propionic acid tert-butyl ester in excellent yield. The tert-butyl ester can then selectively removed by treatment with 4N hydrochloric acid in dioxane to produce 2(S)-methyl-3-(methylsulfonyl)propionic acid as a crystalline acid in very good yield. It is envisioned that variations of the sulfur and carboxylate protecting groups would be acceptable for preparation of 2(S)-methyl-3-(methylsulfonyl)propionic acid and analogs.

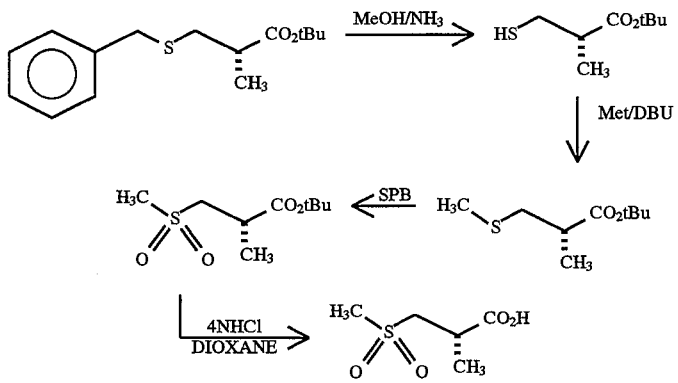

Preparation of Compounds of Formula III

To produce compounds of Formula III, starting with a lactate of the formula:

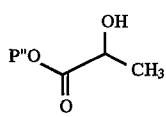

wherein P" represents alkyl and aralkyl radicals, such as, for example, ethyl, methyl, benzyl and the like. The hydroxyl group of the lactate is protected as its ketal by reaction in a suitable solvent system with methyl isopropenyl ether (1,2-methoxypropene) in the presence of a suitable acid. Suitable solvent systems include methylene chloride, tetrahydrofuran and the like as well as mixtures thereof. Suitable acids include $POCl_3$ and the like. It should be noted that well-known groups other than methyl isopropenyl ether can be utilized to form the ketal. The ketal is then reduced with diisobutylaluminum hydride (DIBAL) at $-78°$ C. to produce the corresponding aldehyde which is then treated with ethylidene triphenylphosphorane (Wittig reaction) to produce a compound represented by the formula:

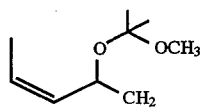

The ketal protecting group is then removed utilizing procedures well-known in the art such as by mild acid hydrolysis. The resulting compound is then esterified with isobutyryl chloride to produce a compound of the formula:

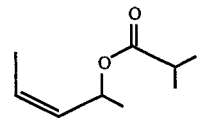

This compound is then treated with lithium diisopropyl amide at $-78°$ C. followed by warming of the reaction mixture to room temperature to effect a Claisen rearrangement ([3,3]) to produce the corresponding acid represented by the formula:

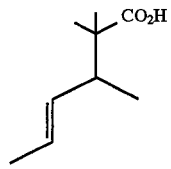

Treatment of the acid with benzyl bromide (BnBr) in the presence of a tertiary amine base, e.g., DBU, produces the corresponding ester which is then cleaved oxidatively to give a trisubstituted succinic acid:

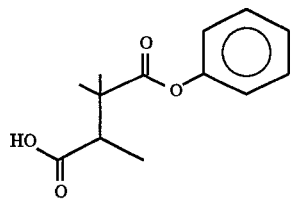

The trisubstituted succinic acid is then coupled to the N-heterocyclic moiety-containing derivative as described above. To produce the free acid, the benzyl ester is removed by hydrogenolysis to produce the corresponding acid. The acid can then be converted to the primary amide by methods well-known in the art.

An alternative method for preparing trisubstituted succinic acids involves reacting an ester of acetoacetic acid represented by the formula:

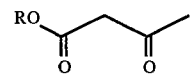

where R is a suitable protecting group, such as methyl, ethyl, benzyl or t-butyl with sodium hydride and a hydrocarbyl halide ($R^{31}X$ or $R^{32}X$) in a suitable solvent, e.g., THF, to produce the corresponding disubstituted derivative represented by the formula:

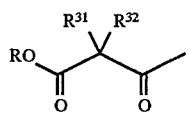

This disubstituted acetoacetic acid derivative is then treated with lithium diisopropyl amide at about −10° C. and in the presence of PhN(triflate)₂ to produce a vinyl triflate of the formula:

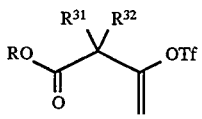

The vinyl triflate is then carbonylated utilizing a palladium catalyst, e.g., Pd(OAc)₂(Ph₃)P, in the presence of an alcohol (R"OH) or water (R"=H) and a base, e.g., triethylamine, in a suitable solvent such as DMF, to produce the olefinic ester or acid of the formula:

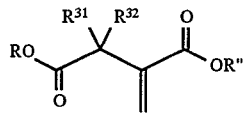

The olefin can then be subsequently asymmetrically hydrogenated, as described above, to produce a trisubstituted succinic acid derivative of the formula:

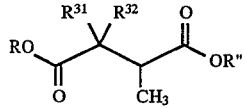

If R" is not H, R" can be removed by either hydrolysis, acidolysis, or hydrogenolysis, to afford the corresponding acid, which is then coupled to the N-heterocyclic moiety-containing derivative as described above and then, optionally, the R group removed to produce the corresponding acid, and optionally, converted to the amide.

Alternatively, one can react the N-heterocyclic moiety-containing derivative with either a suitably monoprotected succinic acid or glutaric acid of the following structures;

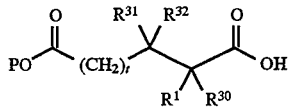

followed by removal of the protecting group and conversion of the resulting acid to an amide. One can also react an anhydride of the following structure:

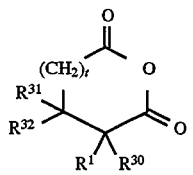

with the N-heterocyclic moiety-containing derivative and then separate any isomers or convert the resulting acid to an amide and then separate any isomers.

Preparation of Compounds of Formula IV

The preparation of compounds of the present invention represented by Formula IV above can be prepared utilizing the general procedure for the preparation of compounds of the present invention represented by Formula I through the preparation of the N-heterocyclic moiety-containing derivative, which is hereby incorporated by reference.

Following preparation of the N-heterocyclic moiety-containing derivative, the amino protecting group P is, or P¹ and P² are, removed under conditions which will not affect the remaining portion of the molecule. These methods are well known in the art and include acid hydrolysis, hydrogenolysis and the like. A preferred method involves removal of the protecting group, e.g., removal of a carbobenzoxy group, by hydrogenolysis utilizing palladium on carbon in a suitable solvent system such as an alcohol, acetic acid, and the like or mixtures thereof. Where the protecting group is N,N-dibenzyl, these groups may be removed by hydrogenolysis utilizing palladium on carbon. Where the protecting group is a t-butoxycarbonyl group, it can be removed utilizing an inorganic or organic acid, e.g., HCl or trifluoroacetic acid, in a suitable solvent system, e.g., dioxane or methylene chloride. The resulting product is the amine salt derivative. Following neutralization of the salt, the amine is then reacted with an acylated amino acid or corresponding analog or derivative thereof represented by the formula:

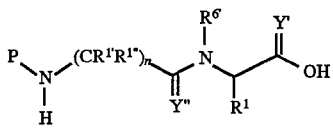

wherein P, R¹, R¹', R¹", R⁶', Y' and Y" are as defined above, to produce the antiviral compounds of the present invention having the formula:

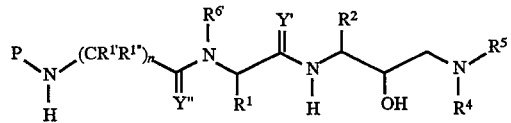

wherein P, R¹, R¹', R¹", R², R⁴, R⁵, R⁶', Y' and Y" are as defined above. Preferred protecting groups in this instance are a benzyloxycarbonyl group or a t-butoxycarbonyl group.

The N-protecting group can be subsequently removed, if desired, utilizing the procedures described above, and then reacted with a carboxylate represented by the formula:

wherein R is as defined above and L is an appropriate leaving group such as a halide. Examples of such carboxylates include acetylchloride, phenoxyacetyl chloride, benzoyl chloride, 2-naphthyloxy carbonyl chloride, and 2-benzofuran carbonyl chloride. A solution of the free amine (or amine acetate salt) and about 1.0 equivalent of the carboxylate are mixed in an appropriate solvent system and optionally treated with up to five equivalents of a base such as, for example, N-methylmorpholine, at about room temperature. Appropriate solvent systems include tetrahydrofuran, methylene chloride or N,N-dimethylformamide, and the like, including mixtures thereof.

Alternatively, a sulfonyl-containing compound represented by the formula:

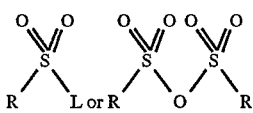

wherein R is as defined above and L is an appropriate leaving group such as halide may be substituted for the afore-mentioned carboxylate.

It is contemplated that for preparing compounds of the Formulas having $R^6$ being other than hydrogen, the compounds can be prepared following the procedure set forth above and, prior to coupling the N-heterocyclic moiety-containing derivative to the respective acid, the derivative carried through a procedure referred to in the art as reductive amination. Thus, a sodium cyanoborohydride and an appropriate aldehyde, such as formaldehyde, acetaldehyde and the like, can be meted with the N-heterocyclic moiety-containing derivative compound at room temperature in order to reductively aminate any of the compounds of Formulas I–IV.

Contemplated equivalents of the respective general formulas set forth above for the antiviral compounds and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, melting points were determined on a Fisher-Johns melting point apparatus and are uncorrected. All reagents were, used as received without purification. All proton and carbon NMR spectra were obtained on either a Varian VXR-300 or VXR-400 nuclear magnetic resonance spectrometer using tetramethysilane as internal standard. Gas chromatograph was performed on a Varian 3400 chromatography system. All instruments were utilized according to the manufacturer's directions.

EXAMPLES

Example 1

Preparation of N-Benzyloxycarbonyl-3(S)-amino-1, 2(S)-epoxy4-phenylbutane

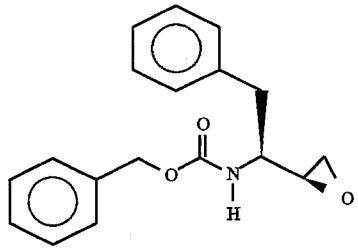

Part A:

To a solution of 75.0 g (0.226 mol) of N-benzyloxycarbonyl-L-phenylalanine chloromethyl ketone in a mixture of 807 mL of methanol and 807 mL, of tetrahydrofuran at −2° C., was added 13.17 g (0.348 mol, 1.54 equiv.) of solid sodium borohydride over one hundred minutes. The solvents were removed in vacuo at 40° C. and the residue dissolved in ethyl acetate (approx. 1L). The solution was washed sequentially with 1M potassium hydrogen sulfate, saturated sodium bicarbonate and then saturated sodium chloride solutions. After drying over anhydrous magnesium sulfate and filtering, the solution was removed in vacuo. To the resulting oil was added hexane (approx. 1L) and the mixture warmed to 60° C. with swirling. After cooling to room temperature, the solids were collected and washed with 2L of hexane. The resulting solid was recrystallized from hot ethyl acetate and hexane to afford 32.3 g (43% yield) of N-benzyloxycarbonyl-3(S)-amino-1-chloro-4-phenyl-2(S)-butanol, mp 150°–151° C. and M+Li$^+$=340. formula:

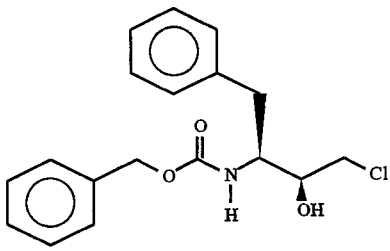

Part B:

To a solution of 6.52 g (0.116 mol, 1.2 equiv.) of potassium hydroxide in 968 mL of absolute ethanol at room temperature, was added 32.3 g (0.097 mol) of N-CBZ-3(S)-amino-1-chloro-4-phenyl-2(S)-butanol, wherein CBZ stands for benzyloxycarbonyl. After stirring for fifteen minutes, the solvent was removed in vacuo and the solids dissolved in methylene chloride. After washing with water, drying over magnesium sulfate ($MgSO_4$), filtering and stripping, one obtains 27.9 g of a white solid. Recrystallization from hot ethyl acetate and hexane afforded 22.3 g (77% yield) of N-benzyloxycarbonyl-3(S)-amino-1, 2(S)-epoxy-4-phenylbutane, mp 102°–103° C. and MH$^+$ 298; formula:

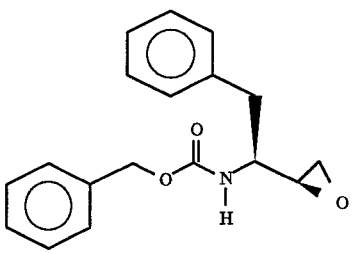

Example 2

Preparation of carbamic acid, [3-[3-[[(1,1-dimethylethyl) amino]carbonyl]octahydro-2(1H)-isoquinolinyl]-2-hydroxy-1-(phenylmethyl)propyl]-, phenylmethyl ester, [3S-[2(1R*,2S*), 3α,4 aβ, 8 aβ]]-. Also known as carbamic acid, [3-[3-[[(1,1-dimethylethyl)amino]carbonyl] decahydro-isoquinolinyl]-2-hydroxy-1-(phenylmethyl) propyl]-, phenylmethyl ester, [3S-[2(1R*,2S*), 3α,4 aβ, 8 aβ]]-.

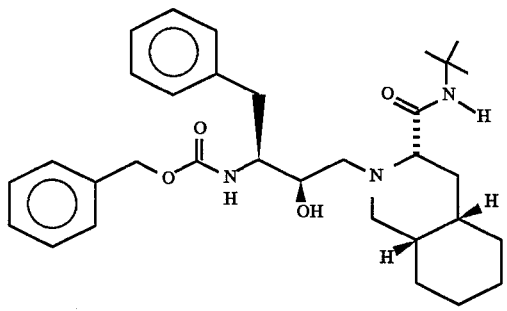

Part A:

L-tetrahydroisoquinoline-2-carboxylic acid (24.83 g, 0.140 mol) was suspended in a solution of 80 mL of 2.5N sodium hydroxide, 80 mL of water, and 80 mL of tetrahydrofuran. To this was added with vigourous stirring, 32.0 g (0.147 mol) of tert-butylpyrocarbonate in 20 mL of tetrahydrofuran. After 1 hour the pH dropped from 13 to 8.2, at pH=7.8 sodium hydroxide (2.5N) was added dropwise to maintain a pH of 8.8. After the pH stabilized, the contents were extracted with diethylether (2×125 mL). The aqueous phase was acidified (pH~2.0) with more HCl, after cooling the solution in an ice bath. The precipitate was extracted with ether, which was then dried over MgSO$_4$, filtered and concentrated to yield 36.8 grams of crude product which needed no purification (95% yield). The product was N-tert-butoxycarbonyl-L-tetrahydroisoquinoline-2-carboxylic acid which has the following formula:

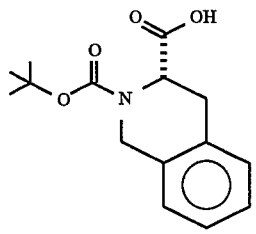

Part B:

N-tert-butoxycarbonyl-L-tetrahydroisoquinoline-2-carboxylic acid (27.7 g, 0.10 moles) was dissolved in 50 mL of dimethylformamide, and to this was added a warmed solution of 21 g of N'-hydroxybenzotriazole in 30 mL of dimethylformamide. The solution was cooled to 10° C. and to this was added 19.1 g (0.10 moles) of 1-(3-dimethylaminopropyl)-2-ethylcarbodiimide hydrochloride (EDC) and the solution stirred for 10–15 minutes, at which time 7.3 g (0.100 moles) of distilled tert-butylamine was added. After 14 hours the solution was concentrated and 200 mL of ethyl acetate was added. The organic layer was washed with 5% aqueous potassium hydrogen sulfate, saturated sodium bicarbonate and brine, dried over magnesium sulfate, filtered, and concentrated to yield a yellow oil, which was crystallized from warm hexane to yield 15.0 grams of a first crop 45.5% yield. The product was N-tert-butoxycarbonyl-S-tetrahydroisoquinoline- 2-carboxylic acid tertbutyl amide which has the following formula:

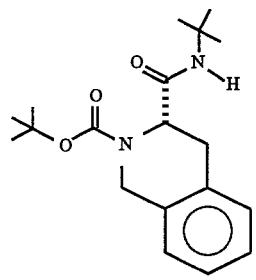

Part C:

N-tert-butoxycarbonyl-S-tetrahydroisoquinoline-2-carboxylic acid tertbutyl amide (10.0 g, 30 mmol) was dissolved in 50 mL of methanol and placed in a Fisher Porter bottle with 3.2 g of wet rhodium (50 wt % H$_2$O, 10 wt % rhodium on carbon). The bottle was purged with nitrogen, and charged with 50 psig hydrogen and heated to 50° C. for 24 hours. The catalyst was removed by filtration and the methanol evaporated to yield a mixture of (S,S,S) desired isomer and (S,R,R) undesired isomer in a 2:1 ratio, respectively. The desired isomer (S,S,S,) was separated by column chromatography on silica gel using a 15–20% ethylacetate hexane gradient elution to yield 6.1 grams of pure isomer (66% yield). The product was N-tert-butyloxycarbonyl-(S,S,S)decahydroisoquinoline-2-carboxylic acid, tert-butylamide which has the following structure:

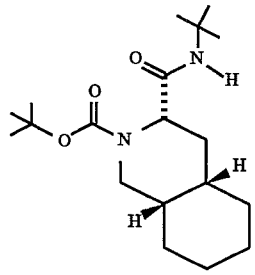

Part D:

N-tert-butyloxycarbonyl-(S,S,S)decahydroisoquinoline-2-carboxylic acid, tert-butylamide (6.3 g, 18.6 mmol) was dissolved in 30 mL of 4N HCl in dioxane and stirred under a nitrogen atmosphere for 1 hour. The solvent was removed and the white solid was suspended in 200 mL of dichloromethane and washed several times with saturated sodium bicarbonate. The dichloromethane (CH$_2$CH$_2$) layer was dried over magnesium sulfate, filtered, and concentrated to yield 3.68 g of freebase (85% yield). The amine product has the following structure:

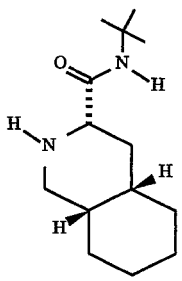

Part E:

The amine from part D (3.68 g, 15.4 mmol) and 4.58 g (15.4 mmol) of epoxide from Example 1 were dissolved in 50 mL of isopropanol and refluxed under a nitrogen atmosphere for 48 hours. The isopropanol was removed and the crude solid was chromatographed on silica gel using methanol methylene chloride eluant to provide 8.0 g of pure product (97% yield) identified as carbamic acid, [3-[3-[[(1, 1-dimethylethyl)amino]-carbonyl]octahydro-2(1H)-isoquinolinyl]-2-hydroxy-1-(phenylmethyl)-propyl]-, phenylmethyl ester, [3S-[2(1R*,2S*), 3α,4 aβ, 8 aβ]]-.

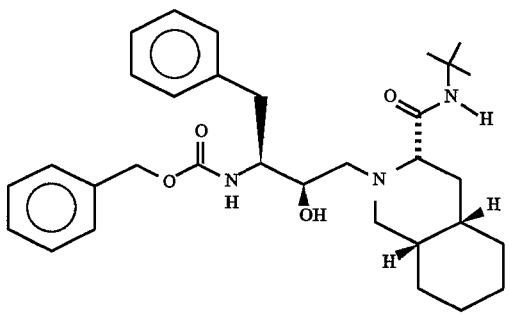

Example 3

Alternate General Procedure for the Synthesis of 1, 3-Diamino-4-Phenyl-2-Ol Derivatives

Step A:

A solution of L-phenylalanine (50.0 g, 0.302 mol), sodium hydroxide (24.2 g, 0.605 mol) and potassium carbonate (83.6 g, 0.605 mol) in water (500 mL) is heated to 97° C. Benzyl bromide (108.5 mL, 0.912 mol) is then slowly added (addition time ~25 minutes). The mixture is then stirred at 97° C. for 30 minutes. The solution is cooled to room temperature and extracted with toluene (2×250 mL). The combined organic layers are then washed with water, brine, dried over magnesium sulfate, filtered and concentrated to give an oil product. The crude product is then used in the next step without purification.

Step B:

The crude benzylated product of the above step is dissolved in toluene (750 mL) and cooled to −55° C. A 1.5M solution of DIABAL-H in toluene (443.9 mL, 0.666 mol) is then added at a rate to maintain the temperature between −55° C. to −50° C. (addition time ~1 hour). The mixture is stirred for 20 minutes at −55° C. The reaction is quenched at −55° C. by the slow addition of methanol (37 mL). The cold solution is then poured into cold (5° C.) 1.5N HCl solution (1.8 L). The precipitated solid (approx. 138 g) is filtered off and washed with toluene. The solid material is suspended in a mixture of toluene (400 mL) and water (100 mL). The mixture is cooled to 5° C., treated with 2.5N NaOH (186 mL) and then stirred at room temperature until the solid is dissolved. The toluene layer is separated from the aqueous phase and washed with water and brine, dried over magnesium sulfate, filtered and concentrated to a volume of 75 mL (89 g). Ethyl acetate (25 mL) and hexane (25 mL) are then added to the residue upon which the alcohol product begins to crystallize. After 30 minutes, an additional 50 mL hexane is added to promote further crystallization. The solid is filtered off and washed with 50 mL hexane to give approximately 35 g of material. A second crop of material can be isolated by refiltering the mother liquor. The solids are combined and recrystallized from ethyl acetate (20 mL) and hexane (30 mL) to give, in 2 crops, approximately 40 g (40% from L-phenylalanine) of analytically pure alcohol product. The mother liquors are combined and concentrated (34 g). The residue is treated with ethyl acetate and hexane which provides an additional 7 g (~7% yield) of slightly impure solid product. Further optimization in the recovery from the mother liquor is probable.

Step C:

A solution of oxalyl chloride (8.4 mL, 0.096 mol) in dichloromethane (240 mL) is cooled to −74° C. A solution of DMSO (12.0 mL, 0.155 mol) in dichloromethane (50 mL) is then slowly added at a rate to maintain the temperature at −74° C. (addition time ~1.25 hours). The mixture is stirred for 5 minutes, followed by addition of a solution of the alcohol (0.074 mol) in 100 mL of dichloromethane (addition time ~20 minutes, temp. −75° C. to −68° C.). The solution is stirred at −78° C. for 35 minutes. Triethylamine (41.2 mL, 0.295 mol) is then added over 10 minutes (temp. −78° to −68° C.) upon which the ammonium salt precipitated. The cold mixture is stirred for 30 minutes and then water (225 mL) is added. The dichloromethane layer is separated from the aqueous phase and washed with water, brine, dried over magnesium sulfate, filtered and concentrated. The residue is diluted with ethyl acetate and hexane and then filtered to further remove the ammonium salt. The filtrate is concentrated to give the desired aldehyde product. The aldehyde was carried on to the next step without purification.

Temperatures higher than −70° C. have been reported in the literature for the Swern oxidation. Other Swern modifications and alternatives to the Swern oxidations are also possible.

A solution of the crude aldehyde 0.074 mol and chloroiodomethane (7.0 mL,, 0.096 mol) in tetrahydrofuran (285 mL) is cooled to −78° C. A 1.6M solution of n-butyllithium in hexane (25 mL, 0.040 mol) is then added at a rate to maintain the temperature at −75° C. (addition time ~15 minutes). After the first addition, additional chloroiodomethane (1.6 mL, 0.022 mol) is added again, followed by n-butyllithium (23 mL, 0.037 mol), keeping the temperature at −75° C. The mixture is stirred for 15 minutes. Each of the reagents, chloroiodomethane (0.70 mL, 0.010 mol) and n-butyllithium (5 mL, 0.008 mol) are added 4 more times over 45 minutes at −75° C. The cooling bath is then removed and the solution warmed to 22° C. over 1.5 hours. The mixture is poured into 300 mL of saturated aq. ammonium chloride solution. The tetrahydrofuran layer is separated. The aqueous phase is extracted with ethyl acetate (1×300 mL). The combined organic layers are washed with brine, dried over magnesium sulfate, filtered and concentrated to give a brown oil (27.4 g). The product could be used in the next step without purification. The desired diastereomer can be purified by recrystallization at a subsequent step. Alternately, the product could be purified by chromatography.

The resulting epoxide can be substituted for the epoxide used in Example 2, Part E.

β-Amino Acid Derivatives

Example 4

Preparation of carbamic acid, [3-[[3-[3-[[(1,1-dimethylethyl)-amino]carbonyl]octahydro-2(1H)-isoquinolinyl]-2-hydroxy-1-(phenyl-methyl)propyl] amino]-2-methyl-3-oxopropyl]-, (4-methoxyphenyl) methylester, [3S-[2[1R*(S*),2S*], 3α, 4 aβ, 8 aβ]]-.

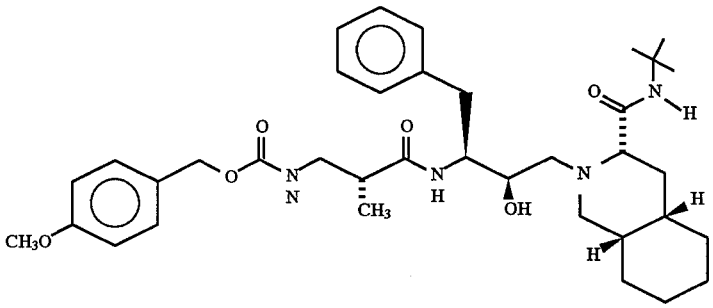

Part A:
A solution of carbamic acid, [3-[3-[[(1,1-dimethylethyl) amino]carbonyl]octahydro-2 (1H) -isoquinolinyl]-2-hydroxy-1-(phenylmethyl) -propyl], phenylmethyl ester, [3S-[2(1R*,2S*), 3α,4 aβ, 8 aβ]]- (1.00 g, 1.87 mmol) in methanol (50 mL) was hydrogenated in the presence of 0.50 g (50% wt) of 10% Pd/charcoal for 19 ½ hours at room temperature and 50 psig of H₂. The catalyst was removed by vacuum filtration through a short plug of celite and the solvent removed in vacuo to give 0.69 g (92%) of a white foam. Subsequently, the crude material was tritrated with diethylether (Et₂O) to give 0.51 g (68%) of a white powder. The amine product has the following formula:

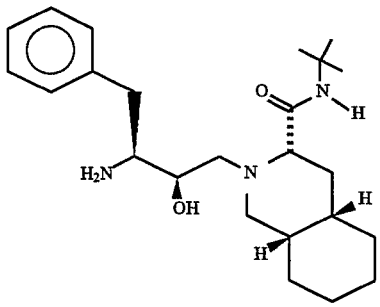

Part B:
N-p-methoxybenzyloxycarbonyl-α-methyl-β-alanine (430.5 mg, 1.6 mmol) was dissolved in 2.0 mL of dimethyl formamide, and to this was added 326 mg (1.5 eq) of N-hydroxybenzotriazole and stirred until the solution was homogeneous. The solution was then cooled to 5° C. and 308 g (1.6 mmol) of 1-(3-dimethylaminopropyl)-3-ethylcarbodiimide was added the reaction stirred for 20 minutes. A solution of 547 mg (1.6 mmol) of the amine from Part A in 5 mL of dimethylformamide (DMF) was added to the solution and stirred for 16 hours. The dimethylformamide was removed by rotory evaporation and replaced with ethylacetate. The organic layer was washed with water and saturated sodium bicarbonate, dried over magnesium sulfate, filtered and concentrated to yield 730 mg of crude product. Flash column chromatography on silica gel using ethylacetate:dichloromethane:ethanol eluant 25:25:1 provided 250 mg of product (25% yield), M+H=651, identified as carbamic acid, [3-[[3-[3-[[(1,1-dimethylethyl)-amino] carbonyl]octahydro-2(1H)-isoquinolinyl]-2-hydroxy-1-(phenyl-methyl) propyl]amino]-2-methyl-3-oxopropyl]-, (4-methoxyphenyl)methyl ester, [3S-[2[1R*(S*),2S*], 3α,4 aβ, 8 aβ]]-.

Example 5

Preparation of 3-(4-Methoxybenzyloxycarbonyl)amino-2 (R)-methylpropionic acid. Also known as N-4-Methoxybenzyloxycarbonyl α-methyl β-alanine (N-Moz-AMBA) and N-p-methoxybenzyloxycarbonyl-α-methyl-β-alanine.

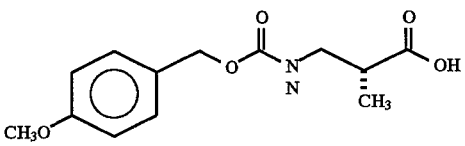

A. Preparation of 4(4-methoxybenzyl)itaconate

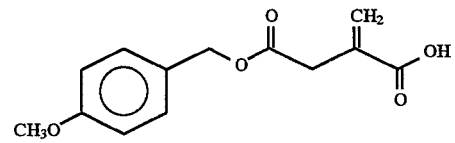

A 5 L three-necked round bottomed flask equipped with constant pressure addition funnel, reflux condenser, nitrogen inlet, and mechanical stirrer was charged with itaconic anhydride (660.8 g, 5.88 mol) and toluene (2300 mL). The solution was warmed to reflux and treated with 4-methoxybenzyl alcohol (812.4 g, 5.88 mol) dropwise over a 2.6 hour period. The solution was maintained at reflux for an additional 1.5 h and then the contents were poured into three 2 L erlenmeyer flasks to crystallize. The solution was allowed to cool to room temperature whereupon the desired mono-ester crystallized. The product was isolated by filtration on a Buchner funnel and air dried to give 850.2 g, 58% of material with mp 83°-85° C., a second crop, 17% was isolated after cooling of the filtrate in an ice bath. $^1$H NMR (CDCl₃) 300 MHz 7.32(d, J=8.7 Hz, 2H), 6.91(d, J=8.7 Hz, 2H), 6.49(s, 1H), 5.85(s, 1H), 5.12(s, 2H), 3.83(s, 3H), 3.40(s, 2H).

B. Preparation of Methyl 4(4-methoxybenzyl) itaconate

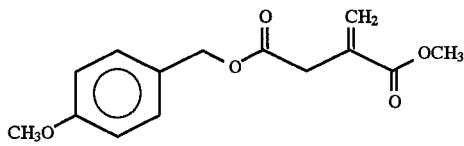

A 5 L three-necked round bottomed flask equipped with reflux condenser, nitrogen inlet, constant pressure addition funnel and mechanical stirrer was charged with 4(4-methoxybenzyl) itaconate (453.4 g, 1.81 mol) and treated with 1,5-diazabicyclo[4.3.0]non-5-ene (275.6 g, 1.81 mol), (DBN), dropwise so that the temperature did not rise above 15° C. To this stirring mixture was added a solution of methyl iodide (256.9 g, 1.81 mol) in 250 mL of toluene from the dropping funnel over a 45 minute period. The solution was flowed to warm to room temperature and stirred for an additional 3.25 hours. The precipitated DBN hydroiodide was removed by filtration, washed with toluene and the filtrate poured into a separatory funnel. The solution was washed with saturated aqueous NaHCO$_3$ (2×500 mL), 0.2N HCl (1×500 mL), and brine (2×500 mL), dried over anhyd. MgSO$_4$, filtered, and the solvent removed in vacuo. This gave a clear colorless oil, 450.2 g, 94% whose NMR was consistent with the assigned structure. $^1$H NMR (CDCl$_3$) 300 MHz 7.30(d, J=8.7 Hz, 2H), 6.90(d, J=8.7 Hz, 2H), 6.34(s, 1H), 5.71(s, 1H), 5.09(s, 2H), 3.82(s, 3H), 3.73(s, 3H), 3.38(s, 2H). $^{13}$C NMR (CDCl$_3$) 170.46, 166.47, 159.51, 133.55, 129.97, 128.45, 127.72, 113.77, 66.36, 55.12, 51.94, 37.64.

C. Preparation of Methyl 4(4-methoxybenzyl) 2(R)-methylsuccinate

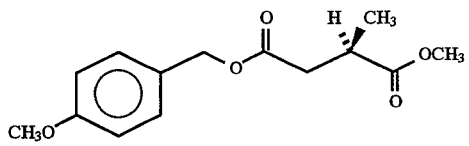

A 500 mL Fisher-Porter bottle was charged with methyl 4(4-methoxybenzyl) itaconate (71.1 g, 0.269 mol), rhodium (R,R) DiPAMP catalyst (204 mg, 0.269 mmol, 0.1 mol %) and degassed methanol (215 mL). The bottle was flushed 5 times with nitrogen and 5 times with hydrogen to a final pressure of 40 psig. The hydrogenation commenced immediately and after ca. 1 hour the uptake began to taper off, after 3 hours the hydrogen uptake ceased and the bottle was flushed with nitrogen, opened and the contents concentrated on a rotary evaporator to give a brown oil that was taken up in boiling iso-octane (ca. 200 mL, this was repeated twice), filtered through a pad of celite and the filtrate concentrated in vacuo to give 66.6 g, 93% of a clear colorless oil, $^1$H NMR (CDCl$_3$ 300 MHz 7.30(d, J=8.7 Hz, 2H), 6.91(d, J=8.7 Hz, 2H), 5.08(s, 2H), 3.82(s, 3H), 3.67(s, 3H), 2.95(ddq, J=5.7, 7.5, 8.7 Hz, 1H), 2.79(dd, J=8.1, 16.5 Hz, 1H), 2.45(dd, J=5.7, 16.5 Hz, 1H), 1.23(d, J=7.5 Hz, 3H).

D. Preparation of Methyl 2(R)-methylsuccinate

A 3 L three-necked round-bottomed flask equipped with a nitrogen inlet, mechanical stirrer, reflux condenser and constant pressure addition funnel was charged with methyl 4(4-methoxybenzyl)2(R)-methylsuccinate (432.6 g, 1.65 mol) and toluene (1200 mL). The stirrer was started and the solution treated with trifluoroacetic acid (600 mL) from the dropping funnel over 0.25 hours. The solution turned a deep purple color and the internal temperature rose to 45° C. After stirring for 2.25 hours the temperature was 27° C. and the solution had acquired a pink color. The solution was concentrated on a rotary evaporator. The residue was diluted with water (2200 mL) and sat. aq. NaHCO$_3$ (1000 mL). Additional NaHCO$_3$ was added until the acid had been neutralized. The aqueous phase was extracted with ethyl acetate (2×1000 mL) to remove the by-products and the aqueous layer was acidified to pH=1.8 with conc. HCl. This solution was extracted with ethyl acetate (4×1000 mL), washed with brine, dried over anhyd. MgSO$_4$, filtered and concentrated on a rotary evaporator to give a colorless liquid 251 g, >100% that was vacuum distilled through a short path apparatus cut 1:bath temperature 120° C. @ >1 mm, bp 25°–29° C.; cut 2: bath temperature 140° C. @ 0.5 mm, bp 95°–108° C., 151 g, [α]$_D$@ 25° C.=+1.38° C.(c=15.475, MeOH), [α]$_D$=+8.48° C. (neat); cut 3: bath temperature 140° C., bp 108° C., 36 g, [α]$_D$ @ 25° C.=+1.49° C.(c=15.00, MeOH), [α]$_D$=+8.98° C. (neat). Cuts 2 and 3 were combined to give 189 g, 78% of product, $^1$H NMR (CDCl$_3$) 300 MHz 11.6(brs, 1H), 3.72(s, 3H), 2.92(ddq, J=5.7, 6.9, 8.0 Hz, 1H, 2.81(dd, J=8.0, 16.8 Hz, 1H), 2.47(dd, J=5.7, 16.8 Hz, 1H), 1.26(d, J=6.9 Hz, 3H).

E. Preparation of Methyl Itaconate

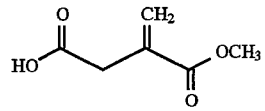

A 50 mL round bottomed flask equipped with reflux condenser, nitrogen inlet and magnetic stir bar was charged with methyl 4(4-methoxybenzyl) itaconate (4.00 g, 16 mmol), 10 mL of toluene and 10 mL of trifluoroacetic acid. The solution was kept at room temperature for 18 hours and then the volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 1.23 g, 75% of pure product, bp 85–87 @ 0.1 mm. $^1$H NMR (CDCl$_3$) 300 MHz 6.34(s, 1H), 5.73(s, 2H), 3.76(s, 3H), 3.38(s, 2H). $^{13}$C NMR (CDCl$_3$)177.03, 166.65, 129.220, 132.99, 52.27, 37.46.

F. Curtius Rearrangement of Methyl 2(R)-methylsuccinate: Preparation of Methyl N-Moz-α-methyl β-alanine

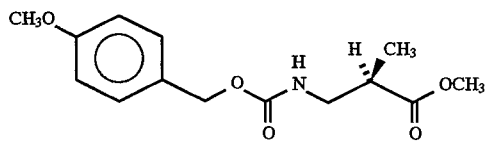

A 5L four necked round bottomed flask equipped with a nitrogen inlet, reflux condenser, mechanical stirrer, constant pressure addition funnel, and thermometer adapter was charged with methyl 2(R)-methylsuccinate (184.1 g, 1.26 mol), triethylamine (165.6 g, 218 mL, 1.64 mol, 1.3 equivalents), and toluene (1063 mL). The solution was warmed to 85° C. and then treated dropwise with a solution of diphenylphosphoryl azide (346.8 g, 1.26 mol) over a period of 1.2 hours. The solution was maintained at that temperature for an additional 1.0 hour and then the mixture was treated with 4-methoxybenzyl alcohol (174.1 g, 1.26 mol) over a 0.33 hours period from the dropping funnel. The solution was stirred at 88° C. for an additional 2.25 hours and then cooled to room temperature. The contents of the flask were poured into a separatory funnel and washed with saturated aqueous NaHCO₃ (2×500 mL), 0.2N HCl (2×500 mL), brine (1×500 mL), dried over anhydrous MgSO₄, filtered, and concentrated in vacuo to give 302.3 g, 85% of the desired product as a slightly brown oil. ₁H NMR (CDCl₃) 300 MHz 7.32(d, J=8.4 Hz, 2H), 6.91(d, J=8.4 Hz, 2H), 5.2(brm, 1H), 5.05(s, 2H), 3.83(s, 3H), 3.70(s, 3H), 3.35(m, 2H), 2.70(m, 2H), 1.20(d, J=7.2 Hz, 3H).

G. Hydrolysis of Methyl N-Moz-α-methyl β-alanine:

Preparation of α-methyl β-alanine Hydrochloride

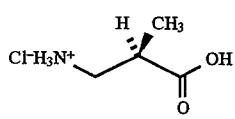

A 5 L three-necked round bottomed flask equipped with a reflux condenser, nitrogen inlet and mechanical stirrer was charged with methyl N-Moz-α-methyl β-alanine (218.6 g, 0.78 mol), glacial acetic acid (975 mL) and 12N hydrochloric acid (1960 mL). The solution was then heated to reflux for 3 h. After the solution had cooled to room temperature (ca. 1 hour) the aqueous phase was decanted from organic residue (polymer) and the aqueous phase concentrated on a rotary evaporator. Upon addition of acetone to the concentrated residue a slightly yellow solid formed that was slurried with acetone and the white solid was isolated by filtration on a Buchner funnel. The last traces of acetone were removed by evacuation to give 97.7 g, 90% of pure product, mp 128.5°–130.5° C. [α]$_D$ @ 25° C.=9.0° C. (c=2.535, Methanol). ¹H NMR (D₂O) 300 MHz 3.29(dd, J=8.6, 13.0 Hz, 1H), 3.16(dd, J=5.0, 13.0 m Hz, 1H), 2.94(ddq, J=7.2, 5.0, 8.6 Hz, 1H), 1.30(d,J=7.2 Hz, 3H); ¹³C NMR (D₂O) 180.84, 44.56, 40.27, 17.49.

H. Preparation of N-Boc α-Methyl β-Alanine

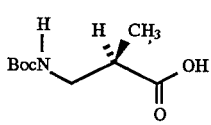

A solution of α-methyl β-alanine hydrochloride (97.7 g, 0.70 mol) in water (1050 mL) and dioxane (1050 mL) the pH was adjusted to 8.9 with 2.9N NaOH solution. This stirring solution was then treated with di-tert-butyl pyrocarbonate (183.3 g, 0.84 mol, 1.2 equivalents) all at once. The pH of the solution was maintained between 8.7 and 9.0 by the periodic addition of 2.5N NaOH solution. After 2.5 h the pH had stabilized and the reaction was judged to be complete. The solution was concentrated on a rotary evaporator (the temperature was maintained at <40° C.). The excess di-tert-butyl pyrocarbonate was removed by extraction with dichloromethane and then the aqueous solution was acidified with cold 1N HCl and immediately extracted with ethyl acetate (4×1000 mL). The combined ethyl acetate extract was washed with brine, dried over anhydrous MgSO₄, filtered and concentrated on a rotary evaporator to give a thick oil 127.3 g, 90% crude yield that was stirred with n-hexane whereupon crystals of pure product formed, 95.65 g, 67%, mp 76°–78° C., [α]$_D$, @ 25° C.=–11.8° C. (c=2.4, EtOH). A second crop was obtained by concentration of the filtrate and dilution with hexane, 15.4 g, for a combined yield of 111.05 g, 78%. ¹H NMR (acetone D₆) 300 MHz 11.7 (brs, 1H), 6.05 (brs 1H), 3.35 (m, 1H), 3.22 (m, 1H), 2.50 (m, 1H), 1.45(s, 9H), 1.19 (d, J=7.3 Hz, 3H); ¹³C NMR (acetone D₆) 177.01, 79.28, 44.44, 40.92, 29.08, 15.50. Elemental analysis calc'd. for C₉H₁₇NO₄: C, 53.19, H, 8.42; N, 6.89. Found: C, 53.36; H, 8.46; N, 6.99.

I. Preparation of N-4-Methoxybenzyloxycarbonyl α-Methyl β-Alanine

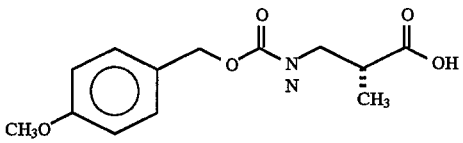

A solution of N-4-methoxybenzyloxycarbonyl α-methyl β-alanine methyl ester (2.81 g, 10.0 mmol) in 30 mL of 25% aqueous methanol was treated with lithium hydroxide (1.3 equivalents) at room temperature for a period of 2 hours. The solution was concentrated in vacuo and the residue taken up in a mixture of water and ether and the phases separated and the organic phase discarded. The aqueous phase was acidified with aqueous potassium hydrogen sulfate to pH=1.5 and then extracted three times with ether. The combined ethereal phase was washed with saturated aqueous sodium chloride solution, dried over anhydrous magnesium sulfate, filtered and concentrated in vacuo to give 2.60 g, 97% of N-4-methoxybenzyloxycarbonyl α-methyl β-alanine (N=Moz-AMBA) which was purified by recrystallization from a mixture of ethyl acetate and hexane to give 2.44 g, 91% of pure product, mp 96°–97° C., MH+=268. ¹H NMR (D₆-acetone/300 MHz) 1.16 (3H, d, J=7.2Hz), 2.70 (1H, m), 3.31 (2H, m), 3.31 (3H, s), 4.99 (2H, s), 6.92 (2H, 4, J=8.7 Hz), 7.13 (2H, d, J=8.7 Hz).

Sulfone Derivatives

Example 6

Preparation of 3-Isoquinolinecarboxamide, N-(1,1-dimethylethyl)decahydro-2-[2-hydroxy-3-[[2-methyl-3-(methylsulfonyl)-1-oxopropyl]amino]-4-phenylbutyl]-, [3S-[2[2S*,3R*(R*)], 3α,4 aβ, 8 aβ]]-.

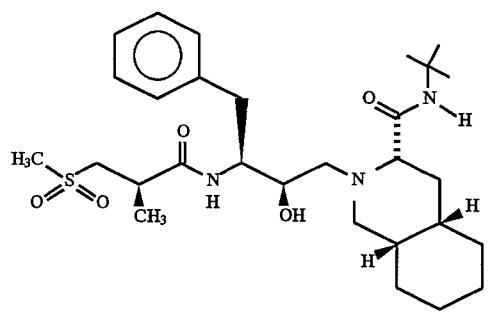

Part A:

A solution of carbamic acid, [3-[3-[[(1,1-dimethylethyl)amino]-carbonyl]octahydro-2(1H)-isoquinolinyl]-2-hydroxy-1-(phenylmethyl)-propyl]-, phenylmethyl ester, [3S-[2(1R*,2S*), 3α,4 aβ, 8 aβ]]- (1.00 g, 1.87 mmol) in methanol (50 mL) was hydrogenated in the presence of 0.50 g (50% wt) of 10% Pd/charcoal for 19½ hours at room temperature and 50 psig of H₂. The catalyst was removed by vacuum filtration through a short plug of celite and the solvent removed in vacuo to give 0.69 g (92%) of a white foam. Subsequently, the crude material was tritrated with diethylether (Et₂O) to give 0.51 g (68%) of a white powder. The amine product has the following formula:

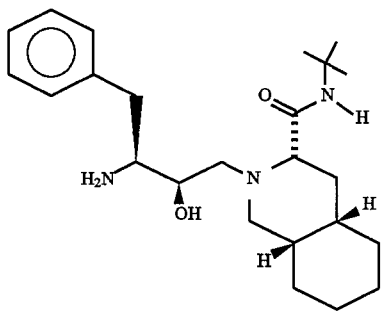

Part B:

To a solution of 230 mg (1.38 mmol) of 2(S)-methyl-3-(methylsulfonyl)propionic acid in anhydrous DMF (4 mL) was added N-hydroxybenzotriazole (HOBt) (290 mg, 2.15 mmol) as a powder and EDC (390 mg, 2.03 mmol) as a powder. The resulting solution was stirred under nitrogen for 10 minutes upon which was added 500 mg (1.24 mmol) of amine from part A in DMF (6 mL) and stirring continued for 17 hours. Subsequently, the reaction mixture was poured into 50% saturated NaHCO₃ (aq) and chilled for 1 hour, upon which a pale precipitate formed, which was filtered, washed with water and dried under reduced pressure to give 430 mg (63%) of a pale powder. The crude material was chromatographed on silica, gel eluating with 5% ethanol in ethyl acetate to give 80 mg (12%) of 3-isoquinolinecarboxamide, N-(1,1-dimethylethyl) decahydro-2-[2-hydroxy-3-[[2-methyl-3-(methylsulfonyl)-1-oxopropyl]amino]-4-phenylbutyl]-, [3S-[2[2S*,3R*(R*)], 3α,4 aβ, 8 aβ]]- as a white powder; mass spectrum, m/e 556 (FAB, M+Li).

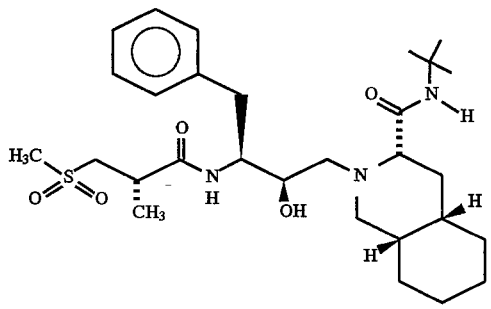

The 2(S)-methyl-3-(methylsulfonyl)propionic acid (see Example 7 for preparation) may be substituted by sulfonyl alkyl acids, for example, 2-(R,S)-methyl-3-(methylsulfonyl) propionic acid (see Example 8 for preparation) and 2-(R,S)-methyl-3(β-phenethylsulfonyl)-propionic acid (see Example 9 for preparation).

Example 7

Preparation of 2(S)-methyl-3-(methylsulfonyl) propionic Acid

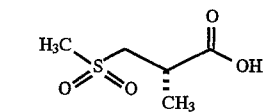

To a solution of 10 g of D-(−)-S-benzoyl-b-mercaptoisobutyric acid t-butyl ester in 20 mL of methanol was bubbled in gaseous ammonia at 0° C. The reaction was allowed to then warm to room temperature, stirred overnight and concentrated in vacuo. The resulting mixture of a solid (benzamide) and liquid was filtered to provide 5.21 g of a pale oil which then solidified. This was identified as 2(S)-methyl-3-mercaptopropionic acid t-butyl ester:

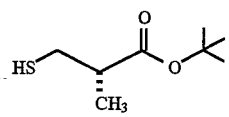

To a solution of 5.21 g of 2(S)-methyl-3-mercaptopropionic acid t-butyl ester in 75 mL of toluene at 0° C. was added 4.50 g of 1,8-diazabicyclo[5.4.0]undec-7-ene (DBU) and 1.94 mL of methyl iodide. After stirring at room temperature for 2.5 hours, the volatiles were removed, ethyl acetate added, washed with dilute hydrochloric acid, water, brine, dried and concentrated to afford 2.82 g of a pale oil, identified as 2(S)-methyl-3-(thiomethyl)propionic acid t-butyl ester:

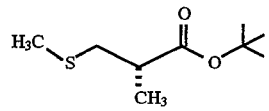

To a solution of 2.82 g of 2(S)-methyl-3-(thiomethyl) propionic acid t-butyl ester in 50 mL of acetic acid was added 5.58 g of sodium perborate and the mixture heated to 55° C. for 17 hours. The reaction was poured into water, extracted with methylene chloride, washed with aqueous sodium bicarbonate, dried and concentrated to afford 2.68 g of 2(S)-methyl-3-(methylsulfonyl)propionic acid t-butyl ester as a white solid:

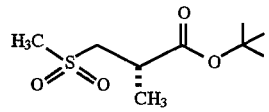

To 2.68 g of 2(S)-methyl-3-(methylsulfonyl)propionic acid t-butyl ester was added 20 mL of 4N hydrochloric acid/dioxane and the mixture stirred at room temperature for 19 hours. The solvent was removed in vacuo to afford 2.18 g of crude product, which was recrystallized from ethyl acetate/hexane to yield 1.44 g of 2(S)-methyl-3-(methylsulfonyl)-propionic acid as white crystals:

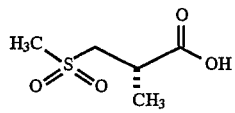

Example 8

Preparation of 2-(R,S)-Methyl-3-(methylsulfonyl)propionic acid by Asymmetric Hydrogenation.

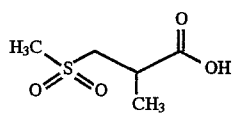

Part A:

A solution of methyl 2-(bromomethyl)-acrylate (26.4 g, 0.148 mol) in 100 mL of methanol was treated with sodium methanesulfinate (15.1 g, 0.148 mol) portion wise over 10 minutes at room temperature. The solution was then stirred at room temperature for a period of 1.25 hours and the solution concentrated in vacuo. The residue was then taken up in water and extracted four times with ethyl acetate. The combined ethyl acetate solution was washed with saturated sodium chloride, dried over anhydrous magnesium sulfate, filtered and concentrated to give a white solid, 20.7 g which was taken up in boiling acetone/methyl tert-butyl ether and allowed to stand whereupon crystals of pure methyl 2-(methylsulfonylmethyl) acrylate 18.0 g, 68% formed, mp 65°–68° C. Formula:

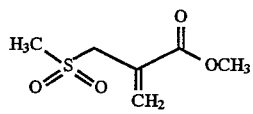

Part B:

A solution of methyl 2-(methylsulfonylmethyl) acrylate (970 mg, 5.44 mmol) in 15 mL of tetrahydrofuran was treated with a solution of lithium hydroxide (270 mg, 6.4 mmol) in 7 mL of water. The solution was stirred at room temperature for 5 minutes and then acidified to pH=1 with 1N aqueous potassium hydrogen sulfate and the solution extracted three times with ethyl acetate. The combined ethyl acetate solution was dried over anhydrous magnesium sulfate, filtered, and concentrated to give 793 mg, 89% of 2-(methylsulfonylmethyl)acrylic acid, mp 147°–149° C.; formula:

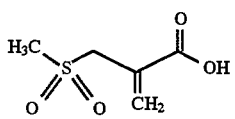

Part C:

A solution of 2-(methylsulfonylmethyl) acrylic acid (700 mg, 4.26 mmol) in 20 mL of methanol was charged into a Fisher-Porter bottle along with 10% palladium on carbon catalyst under a nitrogen atmosphere. The reaction vessel was sealed and flushed five times with nitrogen and then five times with hydrogen. The pressure was maintained at 50 psig for 16 hours and then the hydrogen was replaced with nitrogen and the solution filtered through a pad of celite to remove the catalyst and the filterate concentrated in vacuo to give 682 mg 96% of 2-(R,S)-methyl-3-methylsulfonyl propionic acid; formula:

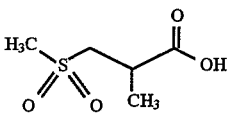

Example 9

Preparation of Sulfones by Michael Addition to Methyl Methacrylate

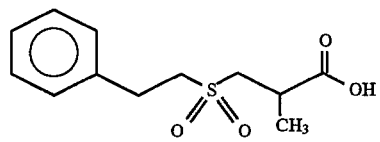

Part A:

A solution of methyl methacrylate (7.25 g, 72.5 mmol) and phenethyl mercaptan (10.0 g, 72.5 mmol) in 100 mL of methanol was cooled in an ice bath and treated with sodium methoxide (100 mg, 1.85 mmol). The solution was stirred under nitrogen for 3 hours and then concentrated in vacuo to give an oil that was taken up in ether and washed with 1N aqueous potassium hydrogen sulfate, saturated aqueous sodium chloride, dried over anhydrous magnesium sulfate, filtered and concentrated to give 16.83 g, 97.5% of methyl 2-(R,S)-methyl-4-thia-6-phenyl hexanoate as an oil. TLC on $SiO_2$ eluting with 20:1 hexane:ethyl acetate (v:v) $R_f$=0.41. Formula:

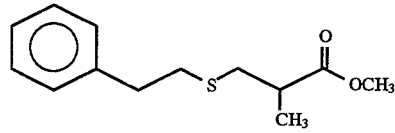

Part B:

A solution of methyl 2-(R,S)-methyl-4-thia-6-phenyl hexanoate (4.00 g, 16.8 mmol) in 100 mL of dichloromethane was stirred at room temperature and treated portion wise with meta-chloroperoxybenzoic acid (7.38 g, 39.2 mmol) over approximately 40 minutes. The solution was stirred at room temperature for 16 hours and then filtered and the filterate washed with saturated aqueous sodium bicarbonate, 1N sodium hydroxide, saturated aqueous sodium chloride, dried over anhydrous magnesium sulfate, filtered, and concentrated to give 4.50 g, 99% of desired sulfone. The unpurified sulfone was dissolved in 100 mL of tetrahydrofuran and treated with a solution of lithium hydroxide (1.04 g, 24.5 mmol) in 40 mL of water. The solution was stirred at room temperature for 2 minutes and then concentrated in vacuo. The residue was then acidified with 1N aqueous potassium hydrogen sulfate to pH=1 and then extracted three times with ethyl acetate. The combined ethyl acetate solution was washed with saturated aqueous sodium chloride, dried over anhydrous magnesium sulfate, filtered and concentrated to give a white solid. The solid was taken up in boiling ethyl acetate/hexane and allowed to stand undisturbed whereupon white needles formed that were isolated by filtration and air dried to give 3.38 g, 79% of 2-(R,S)- methyl-3(β-phenethylsulfonyl)-propionic acid, mp 91°–93° C.; formula:

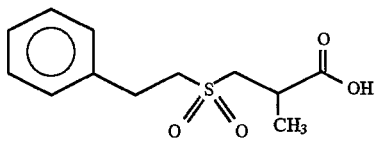

β-Asparagine Derivatives

Example 10

Preparation of butanediamide, $N^4$-[3-[3-[[(1,1-dimethylethyl)-amino]carbonyl]octahydro-2(1H)-isoquinolinyl]-2-hydroxy-1-(phenylmethyl)propyl]-2-[(2-quinolinylcarbonyl)amino]-, [3S[2[1R*(R*),2S*],3α,4 aβ, 8 aβ]].

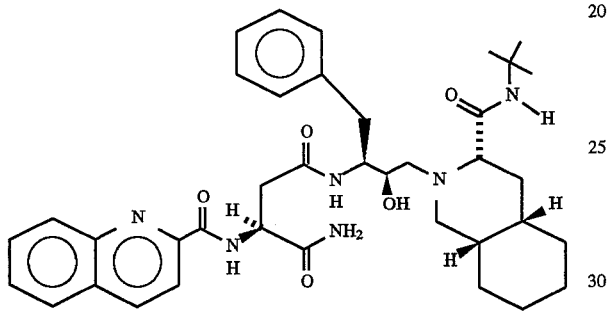

Part A:

A solution of carbamic acid, [3-[3-[[(1,1-dimethylethyl)-amino]carbonyl]octahydro-2(1H)-isoquinolinyl]-2-hydroxy-1-(phenylmethyl)propyl], phenylmethyl ester, [3S-[2(1R*,2S*),3α,4 aβ, 8 aβ]]- (1.2 g, 2.2 mmol) in 50 mL of methanol was charged to a Fisher Porter tube. The contents were purged with nitrogen and 300 mg, 25 wt % of 10% palladium on carbon was carefully added. The solution was charged with 50 psig hydrogen and was vigourously stirred for 2.5 hours. The catalyst was removed by filtration and the solution was concentrated to yield 849 mg (96% yield) of pure amine which has the following formula:

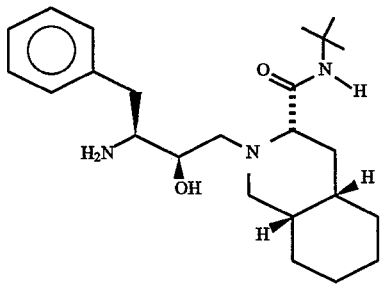

Part B:

N-(2-quinolinylcarbonyl)-L-isoasparagine (366 mg, 1.2 mmol) was dissolved in 4.0 mL, of dry dimethylformamide, and to this was added 250 mg (1.8 mmol) of N-hydroxybenzotriazole. After the solution was homogeneous, 230 mg (1.2 mmol) of 1-(3-Dimethylaminopropyl)-3-ethylcarbodiimide was added and the reaction stirred for 15 minutes. A solution of 510 mg (1.2 mmol) of amine from part A was added in 4.0 mL of dimethylformamide to the solution and stirred for 16 hours.

The majority of solvent was removed and replaced with ethyl acetate. The organic phase was extracted with water, saturated sodium bicarbonate and concentrated to yield 693 mg of white foam. Flash chromatography on silica gel using a gradient elution from 5% to 10% methanol/dichloromethane gave 346 mg of pure product, identified as butanediamide, $N^4$-[3-[3-[[(1,1-dimethylethyl)-amino]carbonyl]octahydro-2(1H)-isoquinolinyl]-2-hydroxy-1-(phenylmethyl)propyl]- 2-[(2-quinolinylcarbonyl)-amino]-, [3S-[2[1R*(R*),2S*], 3α,4aβ, 8aβ]]-. M+Li=677.3. Formula:

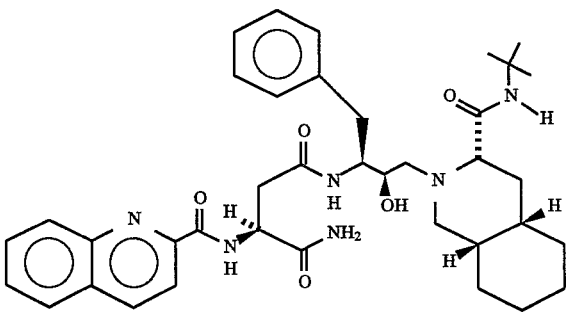

Example 11

Preparation of N-(2-Quinolinylcarbonyl)-L-isoasparagine

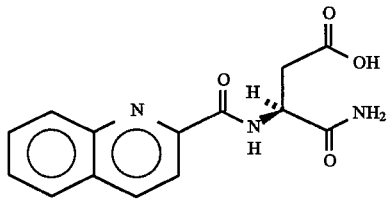

To a solution of 0.50 g (3.78 mmol) of L-isoasparagine in 5.0 mL H₂O containing ~45 mg (1.5 eq) of solid bicarbonate. To this was added a suspension of 1.02 g (3.78 mmol) quinaldic acid, N-hydroxysuccinamide ester in ethylene glycol dimethylether, and the suspension was solubilized by the addition of 10 mL of dimethylformamide. After 3 hours the solution was acidified by the addition of 5% HCl (aqueous) and the product was filtered and washed with water, dried under vacuum to yield 750 mg (70% yield) of N-(2-quinolinylcarbonyl)-L-isoasparagine.

Succinamide Derivatives

Example 12

Preparation of Butanamide, 4-[[3-[3-[[(1,1-dimethylethyl)-amino]carbonyl]octahydro-2 (1H)-isoquinolinyl]-2-hydroxy-1-(phenylmethyl)propyl]amino]-2,2,3-trimethyl-4-oxo-, [3S-[2[1R*(S*),2S*], 3α, 4 aβ, 8 aβ]]-.

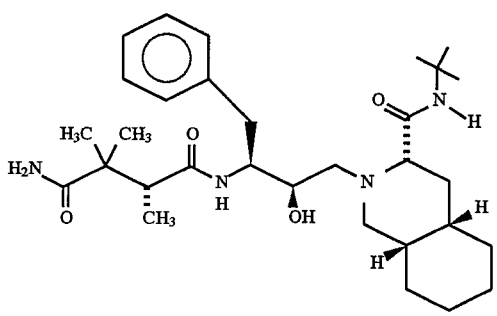

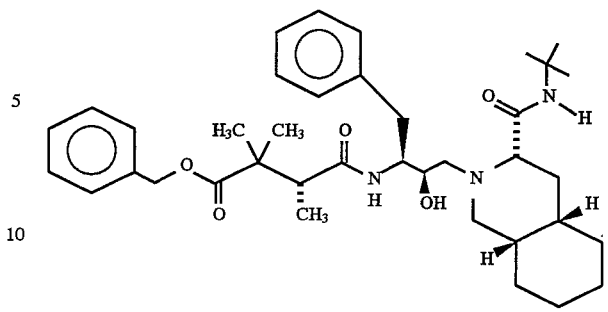

Part A:

A solution of carbamic acid, [3-[3-[[(1,1-dimethylethyl)amino]carbonyl]octahydro-2(1H)-isoquinolinyl]-2-hydroxy-1-(phenylmethyl)propyl]-, phenylmethyl ester, [3S-[2(1R*,2S*), 3α,4aβ,8 a]]-(1.2 g, 2.2 mmol) was dissolved in 50 mL of methanol and charged to a Fisher Porter tube. The contents were purged with nitrogen and 300 mg, 25 wt % of 10% palladium on carbon was carefully added. The solution was charged with 50 psig hydrogen and was vigourously stirred for 2.5 hours. The catalyst was removed by filtration and the solution was concentrated to yield 849 mg (96% yield) of pure amine having the following formula:

Part C:

A mixture of benzyl ester from part B (180 mg, 0.284 mmol), 10% Pd/C (125 mg) in methanol (MeOH) (2 mL) was hydrogenated ($H_2$, 50 psig) at room temperature for 30 minutes. The solid was filtered and was washed with MeOH (3 mL×2). The combined filtrates were concentrated to give 122 mg (79%) acid as a pale yellow solid, [M+H]$^+$=544 and [M+Li]$^+$=550, identified as butanoic acid, 4-[[3-[3-[[(1,1-dimethylethyl)amino]carbonyl]octahydro-2(1H)-isoquinolinyl]-2-hydroxy-1-(phenylmethyl)propyl]amino]-2,2,3-trimethyl-4-oxo-, [3S-[2[1R*(S*),2S*], 3 α,4 aβ, 8 aβ]]-; formula:

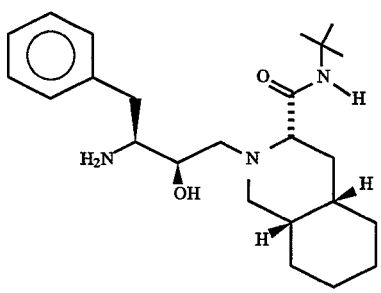

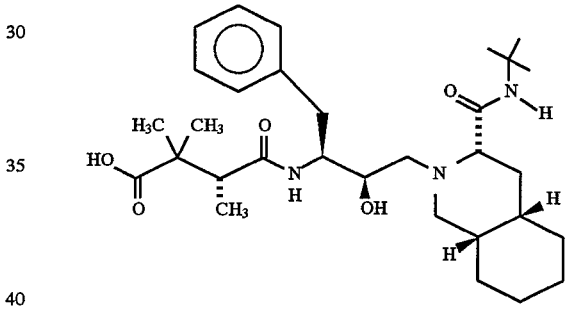

Part B:

To a solution of benzyl 2,2,3(R)-trimethylsuccinate (125 mg, 0.5 mmol) in DMF (1.5 mL) was added HOBt (153 mg, 1.0 mmol). After all the solid was dissolved, the solution was cooled to 0° C. and to this was added EDC (143 mg, 0.75 mmol) and stirring was continued to 2 hours at 0° C. To this cold solution was added 200 mg (0.5 mmol) of amine from part A and stirred at 0° C. for 2 hours and room temperature for 32 hours. The solvents were removed in vacuo (≦40° C.) and the residue was dissolved in ethyl acetate (5 mL). This solution was washed with 60% sat. NaHCO$_3$ (2 mL×2), 5% citric acid (2 mL) and sat. NaCl (2 mL×2). The combined organic layers were dried (Na$_2$SO$_4$) and concentrated to give a white solid. The purification of the crude product by flash chromatography (silica gel, 4% MeOH/CH$_2$Cl$_2$) gave 188 mg (59%) of the desired product as a white solid, [M+Li]$^+$=640, identified as butanoic acid, 4-[[3-[3-[3-[[(1,1-dimethylethyl)amino]carbonyl]octahydro-2(1H)-isoquinolinyl]-2-hydroxy-1-(phenylmethyl)propyl]amino]-2,2,3-trimethyl-4-oxo-, phenylmethyl ester, [3S-[2[1R*(S*),2S*], 3α,4 aβ, 8 aβ]]-; formula:

Part D:

To a solution of acid from part C (120 mg, 0.22 mmol) in DMF (0.5 mL) was added HOBt (68 mg, 0.44 mmol), NH$_4$Cl (11.8 mg, 0.22 mmol) at room temperature. After all the solid was dissolved, to the solution was added EDC (63 mg, 0.33 mmol) at 0° C. and stirred at the temperature for 2 hours. To this cold solution was added 30% NH$_4$OH (0.124 mL, 1.1 mmol) dropwise and the resulting mixture was stirred at 0° C. for 6 hours and at room temperature for 16 hours. The solvents were removed in vacuo (≦40° C.) and the residue was dissolved in ethyl acetate (5 mL). The solution was washed with 60% sat. NaHCO$_3$ (2 mL×2), 5% citric acid (2 mL) and sat. NaCl (2 mL×2). The combined organic layers were dried (Na$_2$SO$_4$) and concentrated to give a white solid. The purification of crude product by flash chromatography (silica gel, 5% MeOH/CH$_2$Cl$_2$) gave 72 mg (60%) of pure amide, [M+H]$^+$=543, identified as Preparation of Butanamide, 4-[[3-[3-[[(1,1-dimethylethyl)amino]carbonyl]octahydro-2 (1H)-isoquinolinyl]-2-hydroxy-1-(phenylmethyl)propyl]amino]-2,2,3-trimethyl-4-oxo-, [3S -[2[1R*(S*),2S*], 3α, 4 aβ, 8 aβ]]-; formula:

41

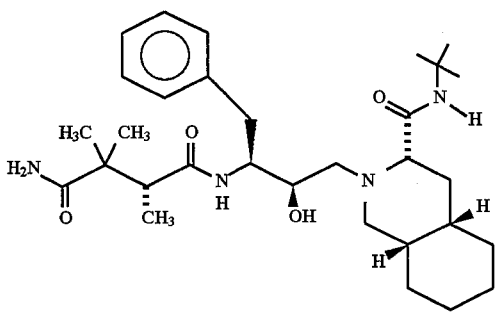

In Example 12, part B, the benzyl 2,2,3(R)-trimethylsuccinate (see Example 13 for preparation) may be substituted by the various succinates, succinamides and itaconamides produced in Examples 13 through 20 infra. in the appropriate amounts the determination of which is within the skill of the art.

Example 13

Preparation of Benzyl 2,2,3(R)-trimethylsuccinate

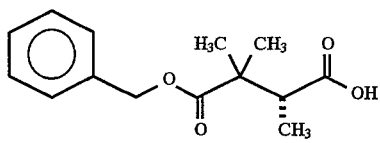

Part A: Preparation of Methyl (S)-lactate, 2-methoxy-2-propyl ether.

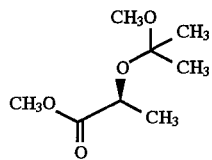

To a mixture of methyl-(S)-(−)-lactate (13.2 g, 100 mmol) and, 2-methoxypropene (21.6 g, 300 mmol) in CH$_2$Cl$_2$ (150 mL) was added POCl$_3$ (about 1.5 mL) at room temperature and the resulting mixture was stirred at this temperature for 16 hours. After the addition of triethylamine (NEt$_3$) (about 2 mL), the solvents were removed in vacuo to give 20.0 g of (98%) desired product.

Part B: Preparation of 2(S)-hydroxypropanal, 2-methoxy-2-propyl ether.

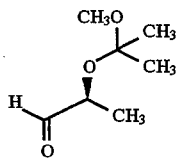

To a solution of compound from Part A (20.0 g) in CH$_2$Cl$_2$ (100 mL) was added diisobutyl aluminum hydride (DIBAL) (65 mL of 1.5M solution in toluene, 97.5 mmol) dropwise at −78° C. for 45 minutes, then stirring was continued at the temperature for another 45 minutes. To this cold solution was added MeOH (20 mL), saturated NaCl solution (10 mL) and allowed the reaction mixture to warm up to room temperature and diluted with ether (200 mL), MgSO$_4$ (150 g) was added and stirred for another 2 hours. The mixture

42 was filtered and the solid was washed twice with ether. The combined filtrates were rotavaped to afford 11.2 g (78%) of the desired aldehyde.

Part C: Preparation of 2(S)-hydroxy-cis-3-butene, 2-methoxy-2-propyl ether.

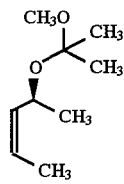

To a suspension of ethyltriphenylphosphonium bromide (28 g, 75.5 mmol) in THF (125 mL) was added potassium bis(trimethylsylyl)amide (KN (TMS)$_2$) (15.7 g, 95%, 75 mmol) in portions at 0° C. and stirred for 1 hour at the temperature. This red reaction mixture was cooled to −78° C. and to this was added a solution of aldehyde from Part B (11 g, 75 mmol) in THF (25 mL). After the addition was completed, the resulting reaction mixture was allowed to warm up to room temperature and stirred for 16 hours. To this mixture was added saturated NH$_4$Cl (7.5 mL) and filtered through a pad of celite with a thin layer of silica gel on the top. The solid was washed twice with ether. The combined filtrates were concentrated in vacuo to afford 11.5 g of crude product. The purification of crude product by flash chromatography (silica gel, 10:1 Hexanes/ethyl acetate) affording 8.2 g (69%) pure alkene.

Part D: Preparation of 2(S)-hydroxy-cis-3-butene.

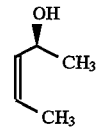

A mixture of alkene from Part C (8.2 g) and 30% aqueous acetic acid (25 mL) was stirred at room temperature for 1 hour. To this mixture was added NaHCO$_3$ slowly to the pH ~7, then extracted with ether (10 mL×5). The combined ether solutions were dried (Na$_2$SO$_4$) and filtered. The filtrate was distilled to remove the ether to give 2.85 g (64%) pure alcohol, m/e=87(M+H).

Part E: Preparation of 2,2,3-trimethyl-hex-(trans)-4-enoic acid.

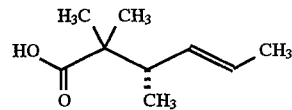

To a mixture of alcohol from Part D (2.5 g, 29 mmol) and pyridine (2.5 mL) in CH$_2$Cl$_2$ (60 mL) was added isobutyryl chloride (3.1 g, 29 mmol) slowly at 0° C. The resulting mixture was stirred at room temperature for 2 hours then washed with H$_2$O (30 mL×2) and sat. NaCl (25 mL). The combined organic phases were dried (Na$_2$SO$_4$), concentrated to afford 4.2 g (93%) ester 2(S)-hydroxy-cis-3-butenyl isobutyrate. This ester was dissolved in THF (10 mL) and was added to a 1.0M lithium diisopropylamide (LDA) solution (13.5 mL of 2.0M LDA solution in THF and 13.5 mL of THF) slowly at −78° C. The resulting mixture was allowed to warm up to room temperature and stirred for 2 hours and diluted with 5% NaOH (40 mL). The organic phase was separated, the aqueous phase was washed with Et₂O (10 mL). The aqueous solution was collected and acidified with 6N HCl to pH~3. The mixture was extracted with ether (30 mL×3). The combined ether layers were washed with sat. NaCl (25 mL), dried (Na₂SO4) and concentrated to afford 2.5 g (60%) of desired acid, m/e=157 (M+H).

Part F: Preparation of benzyl 2,2,3(S)-trimethyl-trans-4-hexenoate.

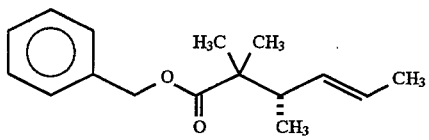

A mixture of acid from Part E (2.5 g, 16 mmol), benzylbromide (BnBr) (2.7 g, 15.8 mmol), K₂CO₃ (2.2 g, 16 mmol), NaI (2.4 g) in acetone (20 mL) was heated at 75° C. (oil bath) for 16 hours. The acetone was stripped off and the residue was dissolved in H₂O (25 mL) and ether (35 mL). The ether layer was separated, dried (Na₂SO₄) and concentrated to afford 3.7 g (95%) of benzyl ester, m/e=247(M+H).

Part G: Preparation of benzyl 2,2,3(R)-trimethylsuccinate.

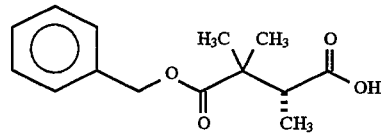

To a well-stirred mixture of KMnO₄ (5.4 g, 34, 2 mmol), H₂O (34 mL), CH₂Cl₂ (6 mL) and benzyltriethylammonium chloride (200 mg) was added a solution of ester from Part F (2.1 g, 8.54 mmol) and acetic acid (6 mL) in CH₂Cl₂ (28 mL) slowly at 0° C. The resulting mixture was stirred at the temperature for 2 hours then room temperature for 16 hours. The mixture was cooled in an ice-water bath, to this was added 6N HCl (3 mL) and solid NaHSO₃ in portions until the red color disappeared. The clear solution was extracted with CH₂Cl₂ (30 mL×3). The combined extracts were washed with sat. NaCl solution, dried (Na₂SO₄) and concentrated to give an oil. This oil was dissolved in Et₂O (50 mL) and to this was added sat. NaHCO₃ (50 mL). The aqueous layer was separated and acidified with 6N HCl to pH~3 then extracted with Et₂O (30 mL×3). The combined extracts were washed with sat. NaCl solution (15 mL), dried (Na₂SO₄) and concentrated to afford 725 mg (34%) of desired acid, benzyl 2,2,3(R)-trimethylsuccinate, m/e=251 (M+H).

Example 14

Preparation of methyl 2,2-dimethyl-3-methyl succinate, (R) and (S) isomers

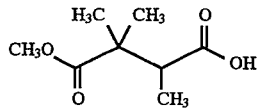

Part A: Preparation of methyl 2,2-dimethyl-3-oxo-butanoate.

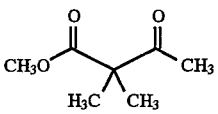

A 250 mL RB flask equipped with magnetic stir bar and N₂ inlet was charged with 100 mL dry THF and 4.57 g (180 mmol) of 95% NaH. The slurry was cooled to −20° C. and 10 g (87 mmol) methyl acetoacetate was added dropwise followed by 11.3 mL (181 mmol) CH₃I. The reaction was stirred at 0° C. for 2 hours and let cool to room temperature overnight. The reaction was filtered to remove NaI and diluted with 125 mL Et₂O. The organic phase was washed with 1×100 L 5% brine, dried and concentrated in vacuo to a dark golden oil that was filtered through a 30 g plug of silica gel with hexane. Concentration in vacuo yielded 10.05 g of desired methyl ester, as a pale yellow oil, suitable for use without further purification.

Part B: Preparation of methyl 2,2-dimethyl-3-0-(trifluoromethanesulfonate)-but-3-enoate.

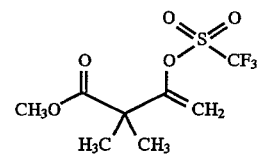

A 250 ml RB flask equipped with magnetic stir bar and N₂ inlet was charged with 80 mL by THF and 5.25 mL (37.5 mmol) diisopropylamine was added. The solution was cooled to −25° C. (dry ice/ethylene glycol) and 15 mL (37.5 mmol) of 2.5M n-butyl lithium (n-BuLi) in hexanes was added. After 10 minutes a solution of 5 g (35 mmol) of methyl 2,2-dimethyl-3-oxo-butanoate from Part A in 8 mL dry THF was added. The deep yellow solution was stirred at −20° C. for 10 minutes then 12.4 g N-phenyl bis (trifluoromethanesulfonimide) (35 mmol) was added. The reaction was stirred @ 10° C. for 2 hours, concentrated in vacuo and partioned between ethyl acetate and sat. NaHCO₃. The combined organic phase was washed with NaHCO₃, brine and concentrated to an amber oil that was filtered through 60 g silica gel plug with 300 mL 5% ethyl acetate/hexane. Concentration in vacuo yielded 9.0 g light yellow oil that was diluted with 65 mL ethyl acetate and washed with 2×50 mL 5% aq. K₂CO₃, 1×10 mL brine, dried over Na₃SO₄ and concentrated in vacuo to yield 7.5 g (87%) vinyl triflate, (m/e=277(M+H) suitable for use without further purification.

Part C: Preparation of methyl 2,2-dimethyl-3-carboxyl-but-3-enoate.

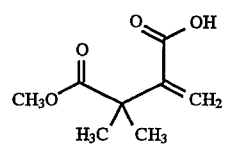

A 250 mL Fisher Porter bottle was charged with 7.5 g (27 mmol) of compound prepared in Part B, 50 mL dry DMF, 360 mg (1.37 mmol) triphenyl phosphine and 155 mg (0.69 mmol) palladium (II) acetate. The reaction mixture was purged twice with N₂ then charged with 30 psig CO. Meanwhile a solution of 20 mL dry DMF and 7.56 mL (54 mmol) NEt₃ was cooled to 0° C. to this was added 2.0 g (43 mmol) of 99% formic acid. The mixture was swirled and added to the vented Fisher Porter tube. The reaction vessel was recharged to 40 psig of CO and stirred 6 hours @ room temperature. The reaction mixture was concentrated in vacuo and pardoned between 100 mL of ethyl acetate and 75 mL 5% aq. $K_2CO_3$. The aqueous phase was washed with 1×40 mL additional ethyl acetate and then acidified with concentrated HCl/ice. The aqueous phase was extracted with 2×70 mL of ethyl acetate and the organics were dried and concentrated to yield 3.5 g (75%) white crystals, mp 72°–75° C., identified as the desired product (m/e=173(M+ H).

Part D: Preparation of methyl 2,2-dimethyl-3-methylsuccinate, isomer #1.

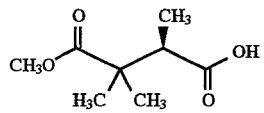

A steel hydrogenation vessel was charged with 510 mg (3.0 mmol) acrylic acid, from Part C, and 6 mg Ru $(acac)_2$ (R-BINAP) in 10 ml degassed MeOH. The reaction was hydrogenated at 50 psig/room temperature for 12 hours. The reaction was then filtered through celite and concentrated to 500 mg clear oil which was shown to be a 93:7 mixture of isomer #1 and #2, respectively as determined by GC analysis using a 50M β-cyclodextrin column (chiral GC): 150° C.—15 min. then ramp 2° C./min.; isomer #1, 17.85 minute retention time, isomer #2, 18–20 minute retention time.

Part E: Preparation of methyl 2,2-dimethyl-3-methylsuccinate, Isomer #2.

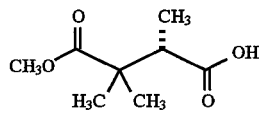

A steel hydrogenation vessel was charged with 500 mg (2.9 mmol) acrylic acid, Part C, and 6 mg Ru(OAc) (acac) (S-BINAP) in 10 mL degassed MeOH. The reaction was hydrogenated at 50 psig/room temperature for 10 hours. The reaction was filtered through celite and concentrated in vacuo to yield 490 mg of product as a 1:99 mixture of isomers #1 and #2, respectively, as determined by chiral GC as above.

Example 15

Preparation of Chiral Succinamides from Itaconic Anhydride

Part A: Preparation of 4-N-benzyl itaconamide.

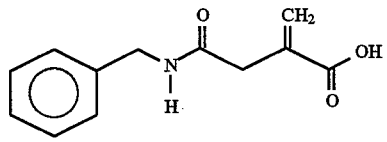

A 500 mL three nicked round bottomed flask equipped with a dropping funnel, mechanical stirrer, nitrogen inlet and reflux condenser was charged with itaconic anhydride (33.6 g, 0.3 mol) and 150 mL of toluene. This solution was added a solution of benzylamine (32.1 g, 0.3 mol) in 50 mL of toluene dropwise over 30 minutes at room temperature. The solution was stirred at this temperature an additional 3 hours and then the solid product isolated by filtration on a Büchner funnel. The crude product, 64.6 g, 98%, was recrystallized from 300 mL of isopropyl alcohol to give after two crops 52.1 g, 79% of pure product, mp 149°–150° C.

Part B: Preparation of 2(R)-Methyl 4-N-benzyl succinamide.

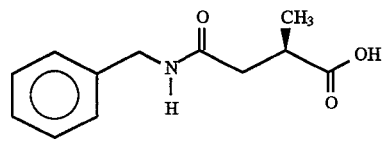

A large Fisher-Porter bottle was charged with the acid from the above reaction (10.95 g, 0.05 mol), rhodium (R,R)-DiPAMP (220 mg, 0.291 mmol) and 125 mL of degassed methanol. The solution was then hydrogenated at 40 psig for 16 hours at room temperature. After the hydrogen uptake ceased, the vessel was opened and the solution concentrated in vacuo to give a yellow solid, 11.05 g, 100%. The product was then taken up in absolute ethanol and allowed to stand whereupon crystals of the desired product formed, 7.98 g, 72%, mp 127°–129° C., $[\alpha]@25°$ C.=+ 14.9° (c=1.332, EtOH), $^1H$ nmr $(CDCl_3)$ 300MHz 7.30(m, 5H), 6.80(brs, 1H), 4.41(d, J=5.8Hz, 2H), 2.94(m, 1H), 2.62(dd, J=8.1, 14.91Hz, 1H), 2.33(dd, J=5.5, 14.9Hz, 1H), 1.23(d, J=7.2Hz, 3H).

Part C: Preparation of 4-N(4-methoxybenzyl)itaconamide.

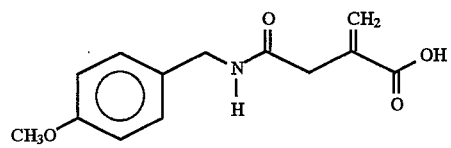

A 500 mL three necked round bottomed flask equipped with a dropping funnel, mechanical stirrer, nitrogen inlet and reflux condenser was charged with itaconic anhydride (44.8 g, 0.4 mol) and 150 mL of toluene. This solution was added a solution of 4-methoxybenzylamine (54.8 g, 0.4 mol) in 50 mL of toluene dropwise over 30 minutes at room temperature. The solution was stirred at this temperature an additional 2 hours and then the solid product isolated by filtration on a Büchner funnel. The crude product was recrystallized from ethyl acetate/ethanol to give after two crops 64.8 g, 65% of pure product, mp 132°–134° C., $^1H$ nmr $(CDCl_3)$ 300MHz 7.09(d, J=9.1Hz, 2H), 6.90(brt, J=5.9Hz, 1H), 6.74(d, J=9.1Hz, 2H), 6.22(s, 1H), 5.69(s, 1H), 4.24(d, J=5.9Hz, 2H), 3.69(s, 3H), 3.15(s, 2H). $^{13}C$ nmr $(CDCl_3)$ 170.52, 169.29, 159.24, 135.61, 131.08, 129.37, 128.97, 114.36, 55.72, 43.37, 40.58.

Part D: Preparation of 2(R)-Methyl 4-N(4-methoxybenzyl) succinamide.

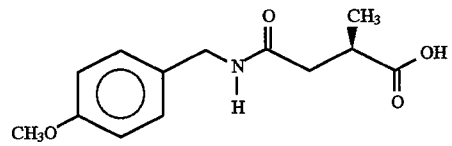

A large Fisher-Porter bottle was charged with the acid from the above reaction (5.00 g, 0.02 mol), rhodium (R,R)-DiPAMP (110 mg, 0.146 mmol) and 50 mL of degassed methanol. The starting acid was not completely soluble initially, but as the reaction progressed the solution became homogeneous. The solution was then hydrogenated at 40 psig for 16 hours at room temperature. After the hydrogen uptake ceased, the vessel was opened and the solution concentrated in vacuo to give a yellow solid. The crude product was then taken up in ethyl acetate and washed three times with sat. aq. NaHCO₃ solution. The combined aqueous extracts were acidified to pH=1 with 3N HCl and then extracted three times with ethyl acetate. The combined ethyl acetate extracts were washed with brine, dried over anhyd. MgSO₄, filtered and concentrated to give the expected product as a white solid, 4.81 g, 95%. This material was recrystallized from a mixture of methyl ethyl ketone/hexane to give 3.80 g, 75% of pure product, $[\alpha]_D$ @ 25° C.=+11.6° (c=1.572, MeOH). $^1$H nmr (CDCl₃) 300MHz 11.9(brs, 1H), 7.18(d, J=9.2Hz, 2H), 6.82(d, J=9.2Hz, 2H), 6.68(brt, J=5.6Hz, 1H), 4.33(d, J=5.6Hz, 2H), 3.77(s, 3H), 2.92(ddq, J=7.9, 5.4, 7.3Hz, 1H), 2.60(dd, J=5.4, 15.0Hz, 1H), 2.30(dd, J=7.9, 15.0Hz, 1H), 1.22(d, J=7.3Hz, 3H).

Example 16

Preparation of Trans-mono-ethyl 1,2-Cyclopropanedicarboxylate

To a solution of 4.60 g (24.7 mmol) of trans-diethyl 1,2-cyclopropanedicarboxylate in 100 mL of 50:50 v:v tetrahydrofuran/water was added 1.24 g (29.6 mmol) of lithium hydroxide. After 17 hours, the tetrahydrofuran was removed in vacuo, the water layer washed with ethyl acetate, acidified with 1N hydrochloric acid and reextracted with ethyl acetate. The organic layer was dried and stripped to afford 2.1 g of crude product. After recrystallization from diethyl ether/hexane and then methylene chloride/hexane, one obtains 1.1 g (28%) of trans-monoethyl 1,2-cyclopropanedicarboxylate, m/e=159 (M+H).

Example 17

Preparation of 2(R)-Methyl-4-benzyl Succinate

Part A:

To a suspension of 24.7 g (0.22 mol) of itaconic anhydride in 100 mL of anhydrous toluene at reflux under a nitrogen atmosphere was added dropwise over 30 minutes 23.9 g (0.22 mol) of benzyl alcohol. The insoluble material dissolved to provide a homogeneous solution which was refluxed for 1.5 hours. The solution was cooled to room temperature, then in an ice bath and the resulting white precipitate collected by filtration to afford 24.8 g (51%) of 4-benzyl itaconate.

Part B:

To a solution of 2.13 g (9.5 mmol) of the product from Part A in 12 mL of methylene chloride at 0° C. was added 4.02 g (29.1 mmol) of para-methoxybenzyl alcohol, 605 mg (4.95 mmol) of N,N-dimethyl 4-aminopyridine, 128 mg of N,N-dimethyl 4-aminopyridine hydrochloride salt and then 2.02 g (4.7 mmol) dicyclohexylcarbodiimide (DCC). After stirring at 0° C. for 1 hour and then room temperature for 2 hours, the precipitate was collected and discarded. The filtrate was washed with 0.5N HCl, sat. NaHCO₃, dried and stripped to afford 4.76 g of crude product. This was chromatographed on silica gel using 0–50% ethyl acetate/hexane to afford 1.24 g of pure 4'-methoxybenzyl-4-benzylitaconate.

Part C:

A solution of 1.24 g (3.65 mmol) of product from Part B and 20 mg of [(R,R)-DiPAMP)cyclooctadienylrhodium] tetrafluoroborate in 30 mL of methanol was thoroughly degassed, flushed with nitrogen and then hydrogen and then stirred under 50 psig of hydrogen for 15 hours. The solution was filtered and stripped, dissolved in methylene chloride and washed with sat. NaHCO₃, dried and stripped to afford 0.99 g of a brown oil. This was then dissolved in 40 mL of methylene chloride, 3 mL of trifluoroacetic acid added and the solution stirred at room temperature for 3.5 hours. Water was added and separated and the organic layer extracted with sat. NaHCO₃. The aqueous layer was acidified and reextracted with ethyl acetate, separated and the organic layer washed with brine, dried and stripped to afford 320 mg (50%) of 2(R)-methyl-4-benzylsuccinic acid.

Example 18

Preparation of 2(S)-Methyl-4-benzyl Succinate

A solution of 1.41 g (4.1 mmol) of 4'-methoxybenzyl 4-benzylitaconate and 25 mg of [(S,S-DiPAMP) cyclooctadienyl-rhodium]tetrafluoroborate in 20 mL of methanol was thoroughly degassed, flushed with nitrogen and then hydrogen and then stirred under 40 psig hydrogen for 72 hours. The solution was filtered and concentrated to provide 1.34 g of a brown off. This was dissolved in 40 mL of methylene chloride and 3 mL of trifluoroacetic acid was added. After stirring for 4 hours, water was added, separated and the organic layer extracted with sat. NaHCO₃. The aqueous layer was separated, reacidified, extracted with ethyl acetate which was separated, washed with brine, dried and stripped to afford 440 mg of 2(S)-methyl-4-benzylsuccinic acid (also known as, 2(S)-Methyl-4-benzyl succinate).

Example 19

Preparation of 3(R)-Methyl-4-benzyl Succinate

Part A:

In a similar manner to the procedure used above in Example 17, Part A, p-methoxybenzyl alcohol was acted with itaconic anhydride in refluxing toluene to provide 4-(4-methoxybenzyl)itaconate.

Part B:

To a solution of 3.30 g (13.2 mmol) of the product from Part A in 17 mL of toluene, was added 2.08 g (13.7 mmol) of 1,8-diazabicyclo[5.4.0]undec-7-ene and then 2.35 g (13.7 mmol of benzyl bromide. After 2 hours, the solution was filtered and the filtrate washed with sat. NaHCO₃, 3N HCl, brine, dried and concentrated to afford 3.12 g of an oil. After chromatography on silica gel using 0–5% ethyl acetate/hexane one obtains 2.19 g (49%) of benzyl 4-(4-methoxybenzyl)itaconate.

Part C:

A solution of 1.22 g (3.6 mmol) of product from Part B and 150 mg of [((R,R-DiPAMP)) cyclooctadienylrhodium] tetrafluoroborate in 15 mL of methanol was thoroughly degassed, flushed with nitrogen and then hydrogen and hydrogenated under 50 psig for 16 hours. The solution was filtered and concentrated to afford 1.2 g of a brown oil. This was dissolved in 5 mL of methylene chloride and 5 mL of toluene and 3 mL of trifluoroacetic acid was added. After 4 hours, the solvents were removed in vacuo, the residue dissolved in methylene chloride, which was then extracted with sat. NaHCO₃. After separation, the aqueous layer was acidified, reextracted with methylene chloride which was then dried and concentrated to afford 470 mg (60%) of 3(R)-methyl-4-benzylsuccinic acid (also known as, 3(R)-methyl-4-benzyl succinate).

Example 20

Preparation of 3(S)-Methyl-4-benzyl Succinate

This was prepared in an identical manner to the previous example (Example 19) except that the asymmetric hydrogenation step was done in the presence of [((S,S-DiPAMP)cyclooctadienyl)rhodium]-tetrafluoroborate as catalyst.

Example 21

Assays

Part A: Enzyme Assay

The compounds of the present invention are effective HIV protease inhibitors. Utilizing an enzyme assay as described below, the compounds set forth in Examples 4, 6, 10, 12 and 12C inhibited the HIV enzyme in an amount ranging from about 3 to about 100% inhibition at a concentration of 10 micromolar. The calculated $IC_{50}$ (inhibiting concentration 50%, i.e., the concentration at which the inhibitor compound reduces enzyme activity by 50%) values are shown in Table 1. The enzyme method is described below. The substrate is 2-aminobenzoyl-Ile-Nle-Phe(p-$NO_2$)-Gln-Arg$NH_2$. The positive control is MVT-101 (Miller, M. et al, Science, 246, 1149 (1989)] The assay conditions are as follows:

Assay buffer: 20 mM sodium phosphate, pH 6.4 20% glycerol 1 mM EDTA 1 mM DTT 0.1% CHAPS The above described substrate is dissolved in DMSO, then diluted 10 fold in assay buffer. Final substrate concentration in the assay is 80 µM.

HIV protease is diluted in the assay buffer to a final enzyme concentration of 12.3 nanomolar, based on a molecular weight of 10,780.

The final concentration of DMSO is 14% and the final concentration of glycerol is 18%, The test compound is dissolved in DMSO and diluted in DMSO to 10× the test concentration; 10 µL of the enzyme preparation is added, the materials mixed and then the mixture is incubated at ambient temperature for 15 minutes. The enzyme reaction is initiated by the addition of 40 µL of substrate. The increase in fluorescence is monitored at 4 time points (0, 8, 16 and 24 minutes) at ambient temperature. Each assay is carried out in duplicate wells.

Part B: CEM Cell Assay

The effectiveness of the compounds tested in Part A was also determined in a CEM cell assay. The HIV inhibition assay method of acutely infected cells is an automated tetrazolium based colorlimetric assay essentially that reported by Pauwles et al, *J. Virol. Methods* 20, 309–321 (1988). Assays were performed in 96-well tissue culture plates. CEM cells, a CD4$^+$ cell line, were grown in RPMI-1640 medium (Gibco) supplemented with a 10% fetal calf serum and were then treated with polybrene (2 µg/mL). An 80 µL volume of medium containing 1×10$^4$ cells was dispensed into each well of the tissue culture plate. To each well was added a 100 µL volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of 5×10$^4$ $TCID_{50}$ per mL ($TCID_{50}$=the dose of virus that infects 50% of cells in tissue culture), and a 20 µL volume of the virus sample (containing 1000 $TCID_{50}$ of virus) was added to wells containing test compound and to wells containing only medium (infected control cells). Several wells received culture medium without virus (uninfected control cells). Likewise, the intrinsic toxicity of the test compound was determined by adding medium without virus to several wells containing test compound. In summary, the tissue culture plates contained the following experiments:

|    | Cells | Drug | Virus |
|----|-------|------|-------|
| 1. | +     | −    | −     |
| 2. | +     | +    | −     |
| 3. | +     | −    | +     |
| 4. | +     | +    | +     |

In experiments 2 and 4, the final concentrations of test compounds were 1, 10, 100 and 500 µg/mL. Either azidothymidine (AZT) or dideoxyinosine (ddI) was included as a positive drug control. Test compounds were dissolved in DMSO and diluted into tissue culture medium so that the final DMSO concentration did not exceed 1.5% in any case. DMSO was added to all control wells at an appropriate concentration.

Following the addition of virus, cells were incubated at 37° C. in a humidified, 5% $CO_2$ atmosphere for 7 days. Test compounds could be added on days 0, 2 and 5 if desired. On day 7, post-infection, the cells in each well were resuspended and a 100 µL sample of each cell suspension was removed for assay. A 20 µL volume of a 5 mg/mL solution of 3-(4,5-dimethylthiazol-2-yl)-2,5-diphenyltetrazolium bromide (MTT) was added to each 100 µL cell suspension, and the cells were incubated for 4 hours at 27° C. in a 5% $CO_2$ environment. During this incubation, MTT is metabolically reduced by living cells resulting in the production in the cell of a colored formazan product. To each sample was added 100 µL of 10% sodium dodecylsulfate in 0.01N HCl to lyse the cells, and samples were incubated overnight. The absorbance at 590 nm was determined for each sample using a Molecular Devices microplate reader. Absorbance values for each set of wells is compared to assess vital control infection, uninfected control cell response as well as test compound by cytotoxicity and antiviral efficacy.

The calculated $EC^{50}$ (effective concentration 50%, i.e., the concentration at which the inhibitor compound reduces cytopathicity by 50%) and $TD^{50}$ (toxic dose 50%, i.e., the concentration at which the inhibitor compound reduces cellular viability by 50%) values for these compounds are also shown in Table 1.

TABLE 1

| | Enzyme Inhibition (IC$_{50}$) | Antiviral Activity in Cell Culture (EC$_{50}$) | Cell Toxicity (TD$_{50}$) |
|---|---|---|---|
| [structure] | 7 nM | 42 nM | 58,000 nM |
| [structure] | 2 nM | 52 nM | 2,000 nM |
| [structure] | 9 nM | 37 nM | 5,000 nM |
| [structure] | 9 nM | 98 nM | 59,000 nM |
| [structure] | 23 nM | 184 nM | 50,000 nM |

Example 22

Acetylated Amino Acid Derivatives

With the aid of the general produce for preparing the compounds according to Formula IV and the analogous procedures in Example 4 (β-amino acid derivatives) and Example 10 (β-asparagine derivative, one skilled in the art can properly select the appropriate acylated amino acid and use these procedures to prepare the compounds listed in Table 2. These compounds are according to Formula IV with $n=1$, $Y'=O$, $Y''=O$, $R^{6'}=H$, $R=CH_3$, $R'=CH_3$, $R^{1'}=H$ and $R^{1''}=H$.

TABLE 2

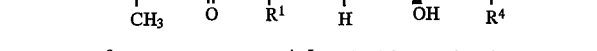

| $R^1$ | $R^2$ | $NR^4R^5$ (derived from amine shown)[a] |
|---|---|---|
| t-butyl | benzyl | N-t-butyl-L-proline amide |
| i-butyl | benzyl | N-t-butyldecahydro-isoquinoline-3-carboxamide |
| sec-butyl | benzyl | N-t-butyldecahydro-isoquinoline-3-carboxamide |
| —C(CH$_3$)$_2$SCH$_3$ | benzyl | N-t-butyldecahydro-isoquinoline-3-carboxamide |
| i-propyl | benzyl | N-t-butyldecahydro-isoquinoline-3-carboxamide |
| propargyl | benzyl | N-t-butyldecahydro-isoquinoline-3-carboxamide |
| t-butyl | benzyl | N-t-butyldecahydro-isoquinoline-3-carboxamide |
| t-butyl | benzyl | N-isobutyl-L-proline amide |
| t-butyl | benzyl | N-t-butyl-piperidine carboxamide |

| $R^1$ | $R^2$ | $NR^4R^5$ |
|---|---|---|
| t-butyl | p-fluorobenzyl | N-t-butyl-L-proline amide |
| i-butyl | p-fluorobenzyl | N-t-butyldecahydro-isoquinoline-3-carboxamide |
| sec-butyl | p-fluorobenzyl | N-t-butyldecahydro-isoquinoline-3-carboxamide |
| —C(CH$_3$)$_2$SCH$_3$ | p-fluorobenzyl | N-t-butyldecahydro-isoquinoline-3-carboxamide |
| i-propyl | p-fluorobenzyl | N-t-butyldecahydro-isoquinoline-3-carboxamide |
| propargyl | p-fluorobenzyl | N-t-butyldecahydro-isoquinoline-3-carboxamide |
| t-butyl | p-fluorobenzyl | N-t-butyldecahydro-isoquinoline-3-carboxamide |
| t-butyl | p-fluorobenzyl | N-isobutyl-L-proline amide |
| t-butyl | p-fluorobenzyl | N-t-butyl-piperidine carboxamide |
| t-butyl | cyclohexyl methyl | N-t-butyl-L-proline amide |
| i-butyl | cyclohexyl methyl | N-t-butyldecahydro-isoquinoline-3-carboxamide |
| sec-butyl | cyclohexyl methyl | N-t-butyldecahydro-isoquinoline-3-carboxamide |
| —C(CH$_3$)$_2$SCH$_3$ | cyclohexyl methyl | N-t-butyldecahydro-isoquinoline-3-carboxamide |
| i-propyl | cyclohexyl methyl | N-t-butyldecahydro-isoquinoline-3-carboxamide |
| propargyl | cyclohexyl methyl | N-t-butyldecahydro-isoquinoline-3-carboxamide |
| t-butyl | cyclohexyl methyl | N-t-butyldecahydro-isoquinoline-3-carboxamide |
| t-butyl | cyclohexyl methyl | N-isobutyl-L-proline amide |
| t-butyl | cyclohexyl methyl | N-t-butyl-piperidine carboxamide |
| t-butyl | n-butyl | N-t-butyl-L-proline amide |
| i-butyl | n-butyl | N-t-butyl-L-proline amide |
| sec-butyl | n-butyl | N-t-butyldecahydro-isoquinoline-3-carboxamide |
| —C(CH$_3$)$_2$SCH$_3$ | n-butyl | N-t-butyldecahydro-isoquinoline-3-carboxamide |
| i-propyl | n-butyl | N-t-butyldecahydro-isoquinoline-3-carboxamide |
| propargyl | n-butyl | N-t-butyldecahydro-isoquinoline-3-carboxamide |
| t-butyl | n-butyl | N-t-butyldecahydro-isoquinoline-3-carboxamide |
| t-butyl | n-butyl | N-isobutyl-L-proline amide |
| t-butyl | n-butyl | N-t-butyl-piperidine carboxamide | t = tert
i = iso
[a]N-heterocyclic moiety results from reaction of amine with epoxide.

Similarly, the compounds according Formula IV, wherein n is 1, $R^2$ is benzyl, $R^6$ is H, $R^1$ is tert-butyl, $R^{6'}$ is H, Y' is O, Y'' is O and $R^{1''}$ is H, listed in Table 3 may be prepared.

TABLE 3

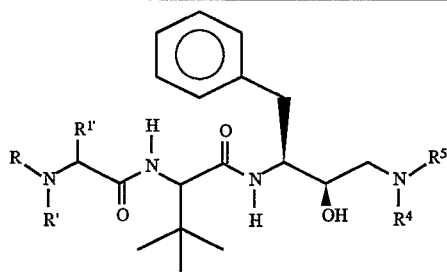

| R1' | R | R' | NR4R5 (derived from amine shown)[a] |
|---|---|---|---|
| methyl | methyl | methyl | N-t-butyl decahydro-isoquinoline-3-carboxamide |
| benzyl | methyl | methyl | N-t-butyl decahydro-isoquinoline-3-carboxamide |
| hydroxymethyl | methyl | methyl | N-t-butyl decahydro-isoquinoline-3-carboxamide |
| 1-hydroxyethyl | methyl | methyl | N-t-butyl decahydro-isoquinoline-3-carboxamide |
| hydrogen | methyl | ethyl | N-i-butyl-L-proline amide |
| hydrogen | methyl | benzyl | N-t-butyl-piperidine carboxamide |

TABLE 3-continued

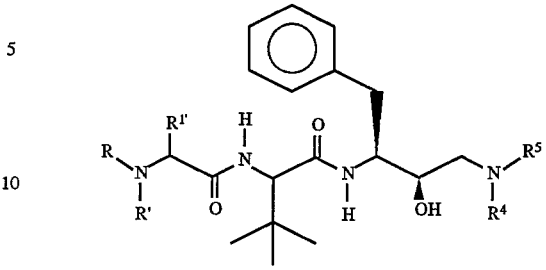

| R1' | R | R' | NR4R5 (derived from amine shown)[a] |
|---|---|---|---|
| hydrogen | R + R' = imidazolyl | | N-t-butyl-piperidine carboxamide |
| hydrogen | R + R' = pyridyl | | N-t-butyl-piperidine carboxamide | t = tert
i = iso
[a] N-heterocyclic moiety results from reaction of amine with epoxide.

Example 23

The compounds shown in Table 4 and 5 can be prepared generally according to the procedure set forth in Examples 4 and the general procedure for preparing compounds according to Formula I.

TABLE 4

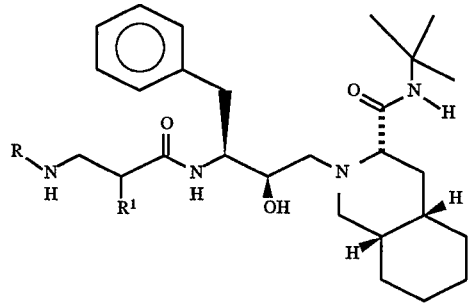

| Entry | $R_1$ | R |
|---|---|---|
| 1 | —CH₃ | 4-methoxybenzyl acetate (CH₃O-C₆H₄-CH₂-O-C(O)-CH₃) |
| 2 | —CH₃ | H₃C-C(O)- |
| 3 | —CH(CH₃)₂ | 4-methoxybenzyl acetate (CH₃O-C₆H₄-CH₂-O-C(O)-CH₃) |
| 4 | —CH(CH₃)₂ | H₃C-C(O)- |

TABLE 4-continued
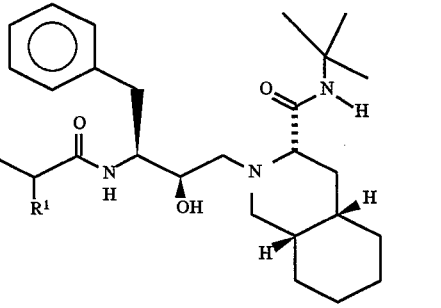
| Entry | R₁ | R |
|---|---|---|
| 5 | —C(CH₃)₃ | 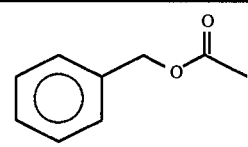 |
| 6 | —CH₃ | 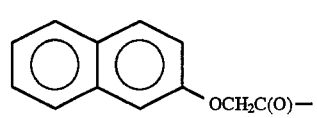 |
| 7 | —CH₃ | 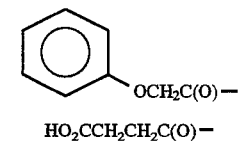 |
| 8 | —CH₃ | HO₂CCH₂CH₂C(O)— |
| 9 | —CH₃ | 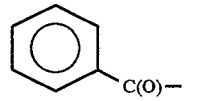 |
| 10 | —CH₃ | CH₃NH—C(O)— |
| 11 | —CH₃ | (CH₃)₂CH—C(O)— |
| 12 | —CH₃ | CH₃OCH₂—C(O)— |
| 13 | —CH₃ | (CH₃)₂NCH₂—C(O)— |
| 14 | —CH₃ | CH₃CH(OH)—C(O)— |
| 15 | | 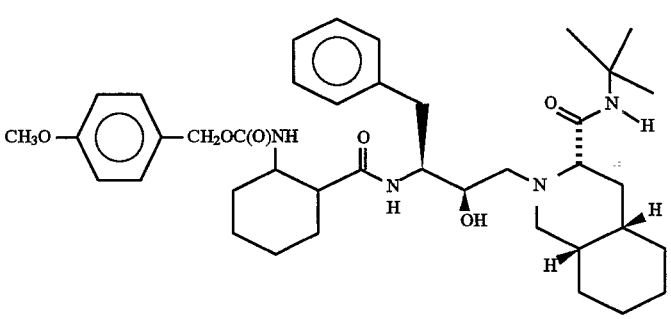 |
| 16 | | 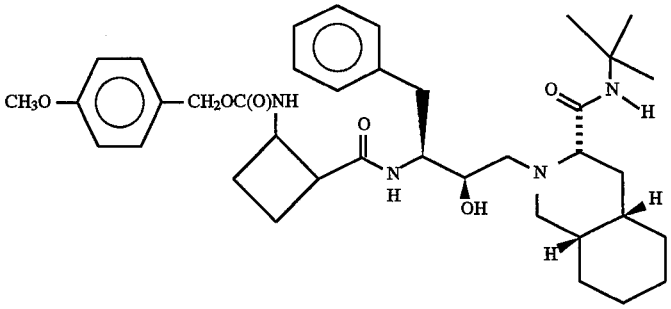 |

TABLE 5

[Structure: compound with R-NH-C(R1')(R1'')-C(R1)-C(O)-NH-CH(CH2Ph)-CH(OH)-CH2-N(decahydroisoquinoline)-C(O)-NH-C(CH3)3]

| R₁ | R¹' | R¹'' | R |
|---|---|---|---|
| H | H | H | benzyl-O-C(O)- |
| H | H | H | CH3-C(O)- (acetyl) |
| H | CH3 | H | 4-methoxybenzyl-O-C(O)- |
| H | CH3 | CH3 | benzyl-O-C(O)- |
| H | H | CO2CH3 | benzyl-O-C(O)- |
| H | H | H | 4-methoxybenzyl-O-C(O)- |
| H | H | H | H2N-C(O)- |
| H | H | CONH2 | Cbz |

Example 24

The compounds shown in Tables 6, 7 and 7A can be prepared generally according to the procedures set forth in Example 6 and the general procedure for preparing compounds according to Formula II.

TABLE 6

[Structure: R'-S(O)2-CH2-CH(CH3)-C(O)-NH-CH(CH2Ph)-CH(OH)-CH2-N(decahydroisoquinoline)-C(O)-NH-C(CH3)3]

R'

$CH_3-$
$CH_3CH_2-$
$CH_3CH_2CH_2-$
$PhCH_2CH_2-$
$PhCH_2-$
$Ph-$
$(CH_3)_2CH-$
$HOCH_2CH_2-$
$C_6H_5CH_2O-C(O)-$
$H_2N-C(O)-CH_2$
$CH_2=CH-CH_2-$

Ph = phenyl

TABLE 7

[Structure: $CH_3-S(O)_2-CH_2-CH(CH_3)-C(O)-NH-CH(R^2)-CH(OH)-CH_2-N(R^4)R^5$]

| R₂ | NR⁴R⁵ |
|---|---|
| benzyl | N-t-butyl-L-proline amide |
| benzyl | N-t-butyl-L-pipecolic acid amide |
| benzyl | N-t-butyldecahydro-isoquinoline-3-carboxamide |

TABLE 7A

[Structure: R'-S(O)2-CH2-CH(R1)-C(O)-NH-CH(CH2Ph)-CH(OH)-CH2-N(decahydroisoquinoline)-C(O)-NH-C(CH3)3]

| R' | R₁ |
|---|---|
| CH3 | -CH(CH3)2 |
| CH3 | -CH(CH3)3 |

Example 25

The compounds shown in Tables 8 and 9 can be prepared generally according to the procedures set forth in Example 12 and in the general procedures for preparing compound according to Formula III.

TABLE 8

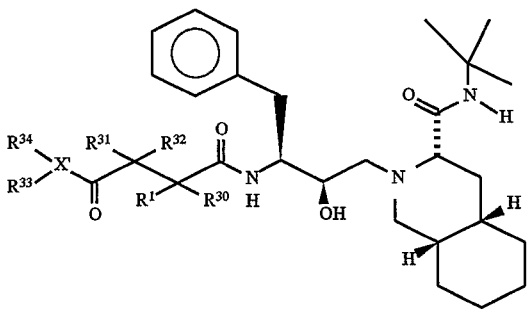

| R¹ | R³⁰ | R³¹ | R³² | X' | R³³ | R³⁴ |
|---|---|---|---|---|---|---|
| H | H | H | H | N | H | H |
| H | H | H | H | O | H | — |
| H | H | H | H | O | CH₃ | — |
| CH₃ | H | H | H | N | H | H |
| CH₃ | H | H | H | O | H | — |
| H | H | CH₃ | H | N | H | H |
| H | H | CH₃ | H | O | H | — |
| CH₃ | CH₃ | H | H | N | H | — |
| CH₃ | CH₃ | H | H | O | H | — |
| CH₃ | CH₃ | H | H | O | CH₂C₆H₄OCH₃ | — |
| H | H | CH₃ | CH₃ | N | H | H |
| H | H | CH₃ | CH₃ | O | H | — |
| H | H | CH₃ | CH₃ | O | CH₂C₆H₄OCH₃ | — |
| CH₃ | H | CH₃ | H | N | H | H |
| CH₃ | H | CH₃ | H | N | H | CH₃ |
| CH₃ | H | CH₃ | H | N | CH₃ | CH₃ |
| CH₃ | H | CH₃ | H | O | H | — |
| CH₃ | H | CH₃ | H | N | H | CH₂C₆H₅OCH₃ |
| OH | H | H | H | N | H | H |
| OH | H | H | H | O | H | H |
| H | H | OH | H | N | H | H |
| H | H | OH | H | O | H | — |
| CH₂ | H | H | H | N | H | H |
| CH₂C(O)NH₂ | H | H | H | N | H | H |
| CH₂C(O)NH₂ | H | H | H | O | H | H |
| CH₂C(O)NH₂ | H | H | H | O | CH₃ | — |
| CH₂CPh | H | H | H | N | H | H |
| CH₃ | H | CH₃ | CH₃ | N | H | H |
| CH₃ | H | CH₃ | CH₃ | O | H | — |
| CH₃ | H | CH₃ | CH₃ | N | H | CH₃ |
| CH₃ | H | Ch₃ | CH₃ | N | CH₃ | CH₃ |

TABLE 9

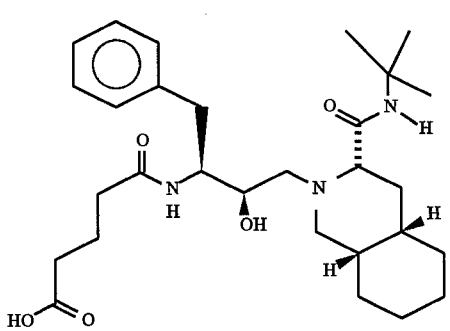

TABLE 9-continued

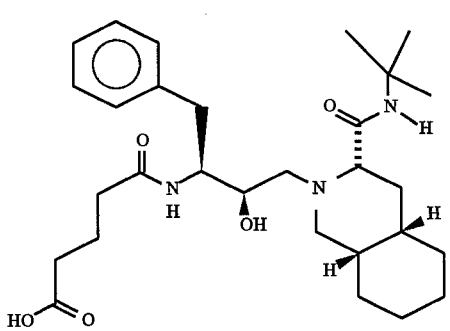

TABLE 9-continued

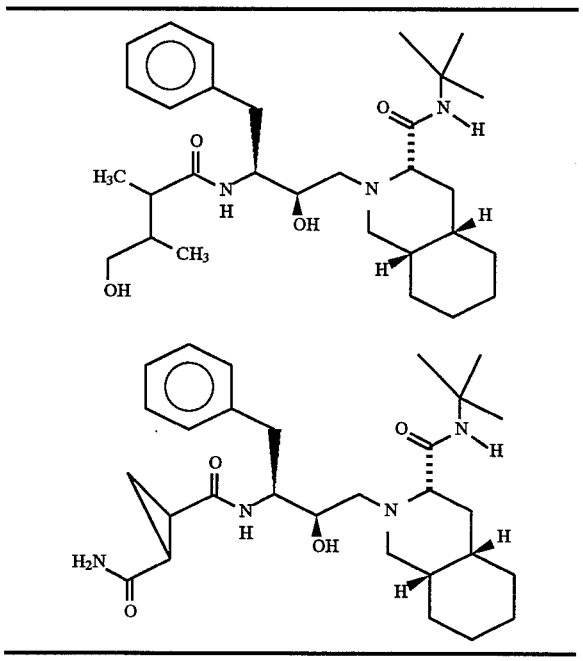

The compounds of the present invention are effective antiviral compounds and, in particular, are effective retroviral inhibitors as shown above. Thus, the subject compounds are effective HIV protease inhibitors. It is contemplated that the subject compounds will also inhibit other viruses such as human T-cell leukemia virus, respiratory syncitial virus, hepadnavirus, cytomegalovirus and picornavirus by the proposed inhibition of post translational proteolytic processing events. Thus, the subject compounds are effective in the treatment and/or prophylaxis of retroviral infections.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Total daily dose administered to a host in single or divided doses may be in mounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

The dosage regimen to give relief from or ameliorate a disease condition (i.e., treatment) or protecting against the further spreading of the infection (i.e., prophylaxis) with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed may vary widely and therefore deviate from the preferred dosage regimen set forth above.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for metal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutically acceptable carriers encompass all the foregoing and the like.

While the compounds of the invention can be administered as the sole active pharmaceutical agent, they can also be used in combination with one or more immunomodulators, antiviral agents or other antiinfective agents. For example, the compounds of the invention can be administered in combination with AZT or with N-butyl-1-deoxynojirimycin for the prophylaxis and/or treatment of AIDS. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

The preceding examples can be repeated with similar success by substituting the genetically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound represented by the formula

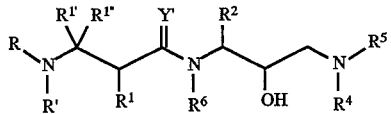

including a pharmaceutically acceptable salt, prodrug or ester thereof, wherein:

R represents hydrogen, alkoxycarbonyl, aryloxycarbonylalkyl, aralkoxycarbonyl, alkylcarbonyl, cycloalkylcarbonyl, cycloalkylalkoxycarbonyl, cycloalkylalkanoyl, alkanoyl, aralkanoyl, aroyl, aryloxycarbonyl, aryloxyalkanoyl, heterocyclylcarbonyl, heterocyclyloxycarbonyl, heteroaralkoxycarbonyl, heterocyclylalkanoyl, heterocyclylalkoxycarbonyl, heteroarylcarbonyl, heteroaryloxycarbonyl, heteroaroyl, alkyl, aryl, aralkyl, aryloxyalkyl, heteroaryloxyalkyl, hydroxyalkyl, alkylaminocarbonyl, arylaminocarbonyl, aralkylaminocarbonyl, aminoalkanoyl, aminocarbonyl, aminocarbonylalkyl, alkylaminoalkylcarbonyl, and mono- and disubstituted aminoalkanoyl radicals wherein the substituents are selected from the group consisting of alkyl, aryl, aralkyl, cycloalkyl, cycloalkylalkyl, heteroaryl, heteroaralkyl, heterocycloalkyl, and heterocycloalkylalkyl radicals, or in the case of disubstituted aminoalkanoyl, said substituents along with the nitrogen atom to which they are attached form a heterocyclyl or heteroaryl radical;

R' represents alkyl, alkenyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals, or R and R' together with the nitrogen to which they are attached form a heterocycloalkyl or heteroaryl radical;

$R^1$ represents hydrogen, —$CH_2SO_2NH_2$, —$CO_2CH_3$, —$CH_2CO_2CH_3$, —$CONH_2$, —$CONHCH_3$, —$CON(CH_3)_2$, —$CH_2CONHCH_3$, —$CH_2CON(CH_3)_2$, alkyl, alkenyl, alkynyl, fluorinated alkyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allothreonine, serine, aspartic acid and beta-cyano alanine side chains;

$R^{1'}$ and $R^{1''}$ independently represent hydrogen and radicals as defined for $R^1$, or one of $R^{1'}$ and $R^{1''}$ together with $R^1$ and the carbon atoms to which they are attached represent a cycloalkyl radical;

$R^2$ represents alkyl, aryl, cycloalkyl, cycloalkylalkyl and aralkyl radicals, which radicals are optionally substituted with a substituent selected from the group consisting of —$NO_2$, —$OR^{15}$, —$SR^{15}$, and halogen radicals, wherein $R^{15}$ represents hydrogen and alkyl radicals;

$R^3$ represents hydrogen, alkyl, alkenyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

Y' represents O, S and $NR^3$;

$R^4$ and $R^5$ together with the nitrogen atom to which they are bonded represent a N-heterocyclic moiety; and $R^6$ represents hydrogen and alkyl radicals.

2. Compound of claim 1; wherein R represents aralkoxycarbonyl and heteroaroyl radicals.

3. Compound of claim 1; wherein R represents carbobenzoxy, 2-benzofurancarbonyl and 2-quinolinylcarbonyl radicals.

4. Compound of claim 1; wherein R represents carbobenzoxy.

5. Compound of claim 1; wherein R represents 2-quinolinylcarbonyl and 2-benzofurancarbonyl radicals.

6. Compound of claim 1; wherein $R^1$ represents alkyl radicals and amino acid side chains selected from the group consisting of asparagine, valine, threonine, allo-threonine, isoleucine, S-methyl cysteine and the sulfone and sulfoxide derivatives thereof, alanine, and allo-isoleucine.

7. Compound of claim 1; wherein $R^1$ represents hydrogen, methyl, trifluoromethyl, t-butyl, isopropyl, hexafluoroisopropyl and sec-butyl radicals, and amino acid side chains selected from the group consisting of asparagine, valine, S-methyl cysteine, allo-iso-leucine, iso-leucine, threonine, serine, aspartic acid, beta-cyano alanine, and allo-threonine side chains.

8. Compound of claim 1; wherein $R^1$ represents methyl and hydrogen.

9. Compound of claim 1; wherein $R^1$ represents amino acid side chains selected from asparagine, valine, alanine and isoleucine side chains.

10. Compound of claim 1; wherein $R^1$ represents amino acid side chains selected from asparagine, isoleucine and valine side chains.

11. Compound of claim 1; wherein $R^1$ represents a methyl radical.

12. Compound of claim 1; wherein $R^1$ represents an isopropyl and sec-butyl radical.

13. Compound of claim 1; wherein $R^2$ represents alkyl, cycloalkylalkyl and aralkyl radicals, which radicals are optionally substituted with halogen radicals and radicals represented by the formula —$OR^9$ and —$SR^9$ wherein $R^9$ represents hydrogen and alkyl radicals.

14. Compound of claim 1; wherein $R^2$ represents alkyl, cycloalkylalkyl and aralkyl radicals.

15. Compound of claim 1; wherein $R^2$ represents aralkyl radicals.

16. Compound of claim 1; wherein $R^2$ represents $CH_3SCH_2CH_2$—, iso-butyl, n-butyl, benzyl, 4-fluorobenzyl, 2-naphthylmethyl and cyclohexylmethyl radicals.

17. Compound of claim 1; wherein $R^2$ represents an n-butyl and iso-butyl radicals.

18. Compound of claim 1; wherein $R^2$ represents benzyl, 4-fluorobenzyl and 2-naphthylmethyl radicals.

19. Compound of claim 1; wherein $R^2$ represents a cyclohexylmethyl radical.

20. Compound of claim 1; wherein $R^1$ and $R^{1'}$ are both hydrogen and $R^{1''}$ represents an alkyl radical having from 1 to about 4 carbon atoms.

21. Compound of claim 1; wherein $R^1$ and $R^{1'}$ are both hydrogen and $R^{1''}$ represents —$CH_2SO_2NH_2$, —$CONH_2$, —$CO_2CH_3$, alkyl and cycloalkyl radicals and amino acid side chains selected from the group consisting of asparagine, S-methyl cysteine and the sulfone and sulfoxide derivatives thereof, histidine, norleucine, glutamine, glycine, allo-isoleucine, alanine, threonine, isoleucine, leucine, tert-leucine, phenylalanine, ornithine, allo-threonine, serine, aspartic acid, beta-cyano alanine and valine side chains.

22. Compound of claim 1; wherein $R^1$ is a methyl radical.

23. Compound of claim 22; wherein R represents an alkanoyl, arylalkanoyl, aryloxyalkanoyl or arylalkyloxylcarbonyl radical.

24. Compound of claim 22; wherein R represents a phenoxyacetyl, 2-naphthyloxyacetyl, benzyloxycarbonyl or p-methoxybenzyloxycarbonyl radical.

25. Compound of claim 1; wherein $R^1$ and $R^{1'}$ are both hydrogen and $R^{1''}$ is $CONH_2$.

26. Compound of claim 25; wherein R represents 2-quinolinylcarbonyl or 2-benzofuranoyl and R' represents hydrogen.

27. Compound of claim 22; wherein R represents an alkylaminocarbonyl and an aralkylaminocarbonyl radical.

28. Compound of claim 22; wherein R represents an N-methylaminocarbonyl and an N-benzylaminocarbonyl radical.

29. The compound of claim 1, wherein the N-heterocyclic moiety is selected from the group consisting of:

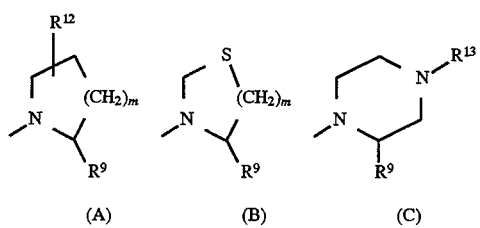

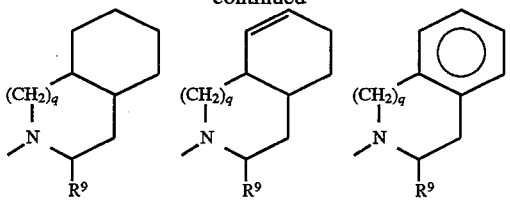

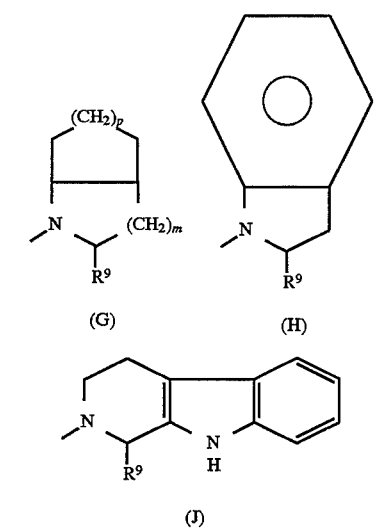

wherein:

$R^9$ represents alkoxycarbonyl, monoalkylcarbamoyl, monoaralkylcarbamoyl, monoarylcarbamoyl or a group of the formula:

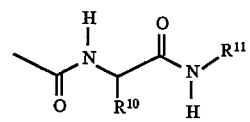

wherein $R^{10}$ and $R^{11}$ each represents alkyl;

$R^{12}$ represents hydrogen, hydroxy, alkoxycarbonylamino or acylamino;

$R^{13}$ represents hydrogen, alkyl, aryl, alkoxycarbonyl or acyl;

m is 1, 2, 3, or 4;

p is 1 or 2; and q is 0, 1 or 2.

30. Compound of claim 29, wherein $R^9$ represents alkoxycarbonyl and monoalkylcarbonoyl.

31. Compound of claim 29, wherein $R^9$ represents —C(O)OC(CH_3)_3$ and —$C(O)NHC(CH_3)_3$.

32. Compound of claim 29, wherein the N-heterocyclic moiety represents a group of formula (D) in which $R^9$ represents N-tertbutylcarbamoyl, and q is 1.

33. Compound of claim 29, wherein the N-heterocyclic moiety is

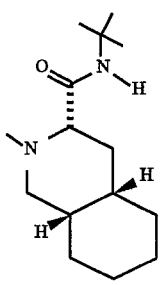

34. A compound of claim 1 which is carbamic acid, [3-[[3-[3-[[(1,1-dimethylethyl)-amino]carbonyl]octahydro-2(1H)-isoquinolinyl]-2-hydroxy-1-(phenyl-methyl)propyl]amino]-2-methyl-3-oxopropyl]-, (4-methoxyphenyl)methyl ester, [3S-[2[1R*(S*),2S*], 3α, 4 aβ, 8 aβ]]-.

35. A compound of claim 1 which is butanediamide, N⁴-[3-[3-[[(1,1-dimethylethyl)-amino]carbonyl]octahydro-2(1H)-isoquinolinyl]-2-hydroxy-1-(phenyl-methyl)propyl]-2-[(2-quinolinylcarbonyl)amino]-[3S[2[1R*(R*), 2S*], 3α, 4 aβ, 8 aβ]]-.

36. A pharmaceutical composition comprising a compound of claim 1 and a pharmaceutically acceptable carrier.

37. A compound represented by the formula:

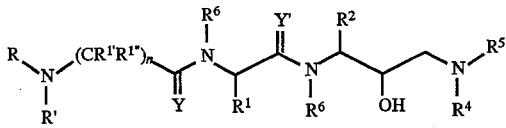

including a pharmaceutically acceptable salt, prodrug or ester thereof, wherein:

R and R' independently represent hydrogen, alkyl, aryl, aralkyl, cycloalkyl, cycloalkylalkyl, heteroaryl, heteroaralkyl, heterocycloalkyl, and heterocycloalkylalkyl radicals, or R and R' along with the nitrogen atom to which they are attached form a heterocyclyl or heteroaryl radical;

n represents 1 or 2;

$R^1$ represents hydrogen, —CH$_2$SO$_2$NH$_2$, —CO$_2$CH$_3$, —CH$_2$CO$_2$CH$_3$, —CONH$_2$, —CONHCH$_3$, —C(CH$_3$)$_2$SCH$_3$, —CON(CH$_3$)$_2$, —CH$_2$CONHCH$_3$, —CH$_2$CON(CH$_3$)$_2$, —C(CH$_3$)$_2$S(O)CH$_3$, —C(CH$_3$)$_2$SO$_2$CH$_3$, alkyl, alkenyl, alkynyl, thioalkyl and cycloalkyl radicals and amino acid side chains selected from the group consisting of asparagine, S-methyl cysteine and the corresponding sulfoxide and sulfone derivatives thereof, glycine, leucine, isoleucine, allo-isoleucine, tert-leucine, alanine, phenylalanine, ornithine, histidine, norleucine, glutamine, valine, threonine, allo-threonine, serine, aspartic acid and beta-cyano alanine side chains;

$R^{1'}$ and $R^{1''}$ independently represent hydrogen and radicals as defined for $R^1$.

$R^2$ represents alkyl, aryl, cycloalkyl, cycloalkylalkyl and aralkyl radicals, which radicals are optionally substituted with a substituent selected from the group consisting of —NO$_2$, —OR$^{15}$, —SR$^{15}$, and halogen radicals, wherein $R^{15}$ represents hydrogen and alkyl radicals;

$R^3$ represents hydrogen, alkyl, alkenyl, hydroxyalkyl, alkoxyalkyl, cycloalkyl, cycloalkylalkyl, heterocycloalkyl, heteroaryl, heterocycloalkylalkyl, aryl, aralkyl, and heteroaralkyl radicals;

Y' and Y" independently represent O, S and NR$^3$;

$R^4$ and $R^5$ together with the nitrogen atom to which they are bonded represent a N-heterocyclic moiety;

$R^6$ and $R^{6'}$ independently represent hydrogen and alkyl radicals.

38. Compound of claim 37; wherein n is 1.

39. Compound of claim 37; wherein $R^1$ represents hydrogen, alkyl, thioalkyl, hydroxyalkyl, alkenyl and alkynyl radicals.

40. Compound of claim 37; wherein $R^1$ represents isopropyl, tert-butyl, isobutyl, sec-butyl, —C(CH$_3$)$_2$SCH$_3$, —C(CH$_3$)$_2$S(O)CH$_3$, —C(CH$_3$)$_2$SO$_2$CH$_3$ and propargyl radicals.

41. Compound of claim 37; wherein $R^1$ represents alkyl radicals having from 1 to about 4 carbon atoms.

42. Compound of claim 37; wherein $R^{1'}$ and $R^{1''}$ independently represent hydrogen, alkyl, hydroxyalkyl and aralkyl radicals.

43. Compound of claim 37; wherein $R^{1'}$ and $R^{1''}$ represent hydrogen.

44. Compound of claim 37; wherein $R^{1'}$ represents hydrogen, methyl, hydroxymethyl, 1-hydroxyethyl and benzyl radicals.

45. Compound of claim 37; wherein $R^{1''}$ is hydrogen.

46. Compound of claim 37; wherein $R^{1'}$ is hydrogen.

47. Compound of claim 37; wherein R and R' independently represent alkyl radicals.

48. Compound of claim 37; wherein R and R' are both methyl radicals.

49. Compound of claim 37; wherein R and R' independently represent alkyl and aryl radicals.

50. Compound of claim 37; wherein R and R' independently represent methyl, ethyl and benzyl radicals.

51. Compound of claim 37, wherein R and R' together with the nitrogen atom to which they are bonded represent a 3 to 8 membered ring heterocyclioalkyl or heteroaryl radical.

52. Compound of claim 37; wherein R and R' together with the nitrogen atom to which they are bonded form a pyrrolidinyl or imidazolyl radicals.

53. Compound of claim 37; wherein $R^2$ represents alkyl, cycloalkyl and aralkyl radicals, which radicals are optionally substituted with halogen radicals and radicals represented by the formula —OR$^{15}$ and —SR$^{15}$ wherein $R^{15}$ represents hydrogen and alkyl radicals.

54. Compound of claim 37; wherein $R^2$ represents n-butyl, cyclohexylmethyl, benzyl and p-fluorobenzyl radicals.

55. Compound of claim 37; wherein $R^2$ represents alkyl, cycloalkylalkyl and aralkyl radicals.

56. Compound of claim 37; wherein $R^2$ represents aralkyl radicals.

57. Compound of claim 37; wherein $R^6$ and $R^{6'}$ independently represent hydrogen.

58. Compound of claim 37; wherein $R^6$ and $R^{6'}$ are hydrogen.

59. Compound of claim 37; wherein Y' and Y" are O.

60. The compound of claim 37, wherein the N-heterocyclic moiety is selected from the group consisting of:

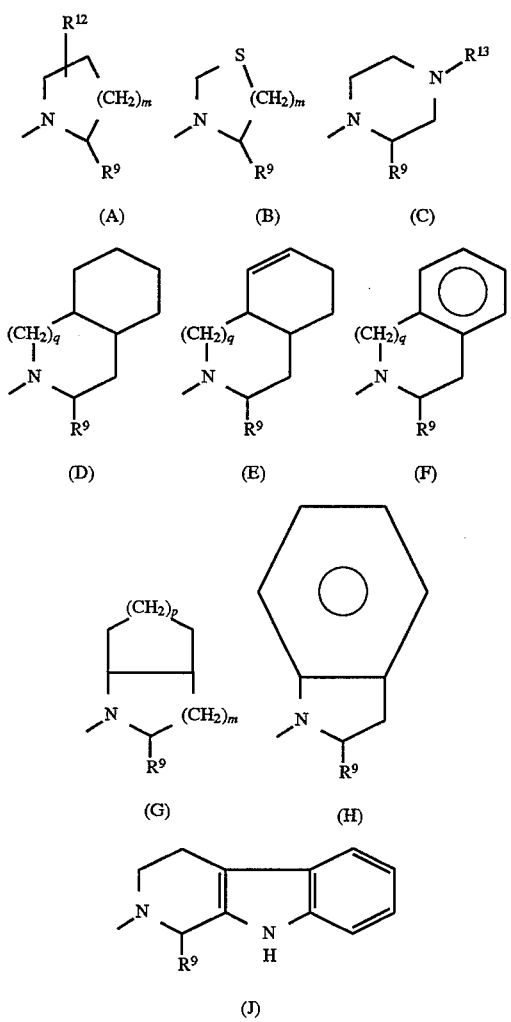

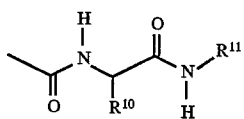

wherein:
R⁹ represents alkoxycarbonyl, monoalkylcarbamoyl, monoaralkylcarbamoyl, monoarylcarbamoyl or a group of the formula:

wherein
$R^{10}$ and $R^{11}$ each represents alkyl;
$R^{12}$ represents hydrogen, hydroxy, alkoxycarbonylamino or acylamino;
$R^{13}$ represents hydrogen, alkyl, aryl, alkoxycarbonyl or acyl;
m is 1, 2, 3, or 4;
p is 1 or 2; and
q is 0, 1 or 2.

61. Compound of claim 60, wherein R⁹ represents alkoxycarbonyl and monoalkylcarbamoyl.

62. Compound of claim 60, wherein R⁹ represents —C(O)OC(CH₃)₃ and —C(O)NHC(CH₃)₃.

63. Compound of claim 60, wherein the N-heterocyclic moiety represents a group of formula (D) in which R₉ represents N-tertbutylcarbamoyl, and q is 1.

64. Compound of claim 60, wherein the N-heterocyclic moiety is:

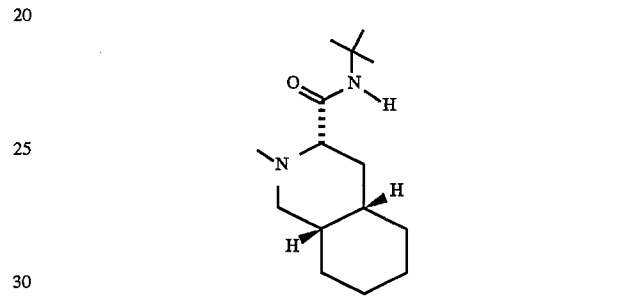

65. A compound of claim 37 which has the following formula:

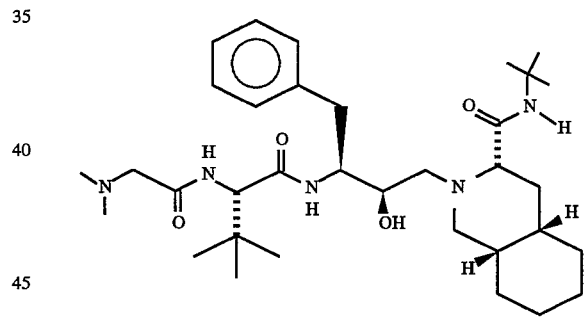

66. A pharmaceutical composition comprising a compound of claim 37 and a pharmaceutically acceptable carrier.

* * * * *